United States Patent
Huddleston et al.

(10) Patent No.: US 11,951,002 B2
(45) Date of Patent: Apr. 9, 2024

(54) APPARATUS AND METHODS FOR VALVE AND TETHER FIXATION

(71) Applicant: Tendyne Holdings, Inc., St. Paul, MN (US)

(72) Inventors: Preston James Huddleston, Maplewood, MN (US); David A. Panus, Maple Grove, MN (US); Theodore Paul Dale, Corcoran, MN (US); Tracee Eidenschink, Wayzata, MN (US); Kevin Patrick Griffin, Elk River, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 192 days.

(21) Appl. No.: 17/209,361

(22) Filed: Mar. 23, 2021

(65) Prior Publication Data
US 2021/0298894 A1  Sep. 30, 2021

Related U.S. Application Data

(60) Provisional application No. 63/001,637, filed on Mar. 30, 2020.

(51) Int. Cl.
*A61F 2/24* (2006.01)

(52) U.S. Cl.
CPC .......... *A61F 2/2418* (2013.01); *A61F 2/2436* (2013.01); *A61F 2220/0016* (2013.01); *A61F 2220/0075* (2013.01); *A61F 2220/0091* (2013.01)

(58) Field of Classification Search
CPC .................................................. A61F 2/2418
See application file for complete search history.

(56) References Cited

U.S. PATENT DOCUMENTS

| | | |
|---|---|---|
| 2,697,008 A | 12/1954 | Ross |
| 3,409,013 A | 11/1968 | Berry |
| 3,472,230 A | 10/1969 | Fogarty et al. |
| 3,476,101 A | 11/1969 | Ross |
| 3,548,417 A | 12/1970 | Kischer |
| (Continued) | | |

FOREIGN PATENT DOCUMENTS

| | | |
|---|---|---|
| CN | 1486161 A | 3/2004 |
| CN | 1961845 A | 5/2007 |
| (Continued) | | |

OTHER PUBLICATIONS

US 9,155,620 B2, 10/2015, Gross et al. (withdrawn)

(Continued)

*Primary Examiner* — Jacqueline Wozniki
(74) *Attorney, Agent, or Firm* — SLEMAN & LUND LLP

(57) ABSTRACT

A valve and tether fixation mechanism includes an anchor, a tether, and a prosthetic heart valve. The anchor may be for anchoring a prosthetic heart valve in a native heart valve. The tether may have a distal end coupled to the anchor. The tether may extend proximally from the anchor and connect to a tensioning mechanism. The prosthetic valve may be configured to translate along the tether. The valve may have a tether connecting portion configured to allow for adjustment of the tension in the tether and affix the prosthetic valve to the tether at a desired tension.

14 Claims, 26 Drawing Sheets

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,852,223 A * | 8/1989 | McCreary ............ F16G 11/101 24/712.7 |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |

(56) References Cited

U.S. PATENT DOCUMENTS

| | | |
|---|---|---|
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,623,224 B2 * | 9/2003 | Schrader ............... B60P 7/0823 410/97 |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Angberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |

(56) References Cited

U.S. PATENT DOCUMENTS

| | | | |
|---|---|---|---|
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,579,963 B2 | 11/2013 | Tabor |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,364,325 B2 | 6/2016 | Alon et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0083562 A1* | 7/2002 | Lerra .................. A44B 11/266 24/115 G |
| 2002/0101071 A1* | 8/2002 | Ayliffe .................. A63C 11/00 280/809 |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078465 A1* | 4/2003 | Pai ....................... A61B 17/064 600/16 |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0055606 A1 | 3/2004 | Hendricksen et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0096735 A1 | 5/2005 | Hojeibane et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288763 A1 | 12/2005 | Andreas et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |

(56) References Cited

U.S. PATENT DOCUMENTS

| | | |
|---|---|---|
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0122633 A1* | 6/2006 | To ................ A61B 17/0682 606/139 |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2006/0287719 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0088431 A1 | 4/2007 | Bourang et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0244556 A1* | 10/2007 | Rafiee ................ A61F 2/2466 623/2.37 |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0057767 A1* | 3/2008 | O'Rourke ........ H01R 13/6691 439/345 |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Amphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0054976 A1 | 2/2009 | Tuval et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0173455 A1* | 7/2009 | Hartley ................ A45F 5/02 160/127 |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1* | 11/2009 | Rowe ................ A61F 2/2418 623/2.18 |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |

(56) References Cited

U.S. PATENT DOCUMENTS

| | | |
|---|---|---|
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0234940 A1 | 9/2010 | Dolan |
| 2010/0249489 A1 | 9/2010 | Jarvik |
| 2010/0249923 A1 | 9/2010 | Alkhatib et al. |
| 2010/0257701 A1* | 10/2010 | Gammell ............... A43C 7/00 24/115 G |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015714 A1* | 1/2011 | Atkinson ............... A61N 1/057 607/126 |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0046712 A1 | 2/2011 | Melsheimer et al. |
| 2011/0054519 A1 | 3/2011 | Neuss |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0185476 A1* | 8/2011 | Boisseau ............... A41D 1/08 2/243.1 |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0301703 A1 | 12/2011 | Glazier |
| 2011/0319988 A1 | 12/2011 | Schankereli et al. |
| 2011/0319989 A1 | 12/2011 | Ane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0078347 A1 | 3/2012 | Braido et al. |
| 2012/0083874 A1 | 4/2012 | Dale et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0239142 A1 | 9/2012 | Liu et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0059747 A1 | 3/2013 | Mann et al. |
| 2013/0066341 A1 | 3/2013 | Ketai et al. |
| 2013/0079873 A1* | 3/2013 | Migliazza ............... A61F 2/2412 623/2.17 |
| 2013/0110228 A1 | 5/2013 | Braido |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0268064 A1 | 10/2013 | Duffy |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0005767 A1 | 1/2014 | Glazier et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0128963 A1 | 5/2014 | Quill et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0298621 A1* | 10/2014 | Anfuso ............... F16G 11/101 24/115 G |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0316518 A1 | 10/2014 | Kheradvar et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105817 A1* | 4/2015 | Marchand ........ A61B 17/12113 606/194 |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |

(56) References Cited

U.S. PATENT DOCUMENTS

| | | |
|---|---|---|
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305867 A1 | 10/2015 | Liu et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1* | 7/2017 | Christianson ......... A61F 2/2457 |
| 2017/0252153 A1 | 9/2017 | Chau et al. |
| 2017/0258589 A1 | 9/2017 | Pham et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0312078 A1 | 11/2017 | Krivoruchko |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0153262 A1* | 6/2018 | Shimizu ............... F16G 11/106 |
| 2018/0193138 A1 | 7/2018 | Vidlund |
| 2018/0263618 A1 | 9/2018 | Vidlund et al. |
| 2018/0289473 A1* | 10/2018 | Rajagopal ............ A61F 2/2418 |
| 2018/0289478 A1* | 10/2018 | Quill .................... A61F 2/2466 |
| 2018/0289480 A1* | 10/2018 | D'ambra ............... A61F 2/2445 |
| 2019/0117401 A1* | 4/2019 | Cortez, Jr. ............ A61F 2/2466 |
| 2020/0022810 A1 | 1/2020 | Christianson et al. |
| 2020/0187596 A1* | 6/2020 | Krout ..................... A43C 11/24 |
| 2020/0318712 A1* | 10/2020 | Aihara ................... B65D 33/28 |
| 2021/0022855 A1* | 1/2021 | Tegels ................... A61F 2/2466 |
| 2021/0030535 A1* | 2/2021 | Liu ........................ A61F 2/2418 |
| 2021/0046348 A1* | 2/2021 | Arnold ................... A63B 69/36 |
| 2021/0128298 A1* | 5/2021 | Rengarajan ........... A61F 2/2421 |
| 2021/0169645 A1* | 6/2021 | Dale ...................... A61F 2/2427 |
| 2021/0177585 A1* | 6/2021 | deHoog ................. A61F 2/2418 |
| 2021/0186687 A1* | 6/2021 | Danielson .......... A61B 17/0401 |
| 2021/0298899 A1* | 9/2021 | Huddleston ........... A61F 2/2433 |
| 2022/0008201 A1* | 1/2022 | Passman ................. A61F 2/246 |
| 2022/0023035 A1* | 1/2022 | Rajagopal ............. A61F 2/2418 |
| 2022/0104941 A1* | 4/2022 | Rajagopal ............. A61F 2/2466 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2007509700 A | 4/2007 |
| JP | 2008504078 A | 2/2008 |
| JP | 2008541863 A | 11/2008 |
| JP | 2009511229 A | 3/2009 |
| JP | 2009514628 A | 4/2009 |
| JP | 2009519783 A | 5/2009 |
| JP | 2012504031 A | 2/2012 |
| JP | 2012518465 A | 8/2012 |
| JP | 2012519024 A | 8/2012 |
| JP | 2013512765 A | 4/2013 |
| JP | 2013525039 A | 6/2013 |
| JP | 2013538086 A | 10/2013 |
| JP | 2014513585 A | 6/2014 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 2001035878 A2 | 5/2001 |
| WO | 0149213 A2 | 7/2001 |
| WO | 200149213 A3 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 200176510 A2 | 10/2001 |
| WO | 2001082840 A1 | 11/2001 |
| WO | 2002004757 A1 | 1/2002 |
| WO | 2002022054 A1 | 3/2002 |
| WO | 2002032321 A2 | 4/2002 |
| WO | 0236048 A1 | 5/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 02076348 A1 | 10/2002 |
| WO | 2003003943 A2 | 1/2003 |

(56) References Cited

FOREIGN PATENT DOCUMENTS

| | | | |
|---|---|---|---|
| WO | 2003030776 A2 | 4/2003 | |
| WO | 2003047468 A1 | 6/2003 | |
| WO | 2003049619 A2 | 6/2003 | |
| WO | 2004019825 A1 | 3/2004 | |
| WO | 2005102181 A1 | 11/2005 | |
| WO | 2006005082 A2 | 1/2006 | |
| WO | 2006014233 A2 | 2/2006 | |
| WO | 2006034008 A2 | 3/2006 | |
| WO | 2006064490 A1 | 6/2006 | |
| WO | 2006070372 A2 | 7/2006 | |
| WO | 2006105009 A1 | 10/2006 | |
| WO | 2006113906 A1 | 10/2006 | |
| WO | 2006127756 A2 | 11/2006 | |
| WO | WO-2007056583 A1 * | 5/2007 | ......... A61B 17/0401 |
| WO | 2007081412 A1 | 7/2007 | |
| WO | 2007100408 A2 | 9/2007 | |
| WO | 2008005405 A2 | 1/2008 | |
| WO | 2008035337 A2 | 3/2008 | |
| WO | 2008091515 A2 | 7/2008 | |
| WO | 2008125906 A2 | 10/2008 | |
| WO | 2008147964 A1 | 12/2008 | |
| WO | 2009024859 A2 | 2/2009 | |
| WO | 2009026563 A2 | 2/2009 | |
| WO | 2009045338 A1 | 4/2009 | |
| WO | 2009094500 A1 | 7/2009 | |
| WO | 2009132187 A1 | 10/2009 | |
| WO | 2010022138 A2 | 2/2010 | |
| WO | 2010090878 A2 | 8/2010 | |
| WO | 2010098857 A1 | 9/2010 | |
| WO | 2010121076 A2 | 10/2010 | |
| WO | 2011017440 A2 | 2/2011 | |
| WO | 2011022658 A1 | 2/2011 | |
| WO | 2011069048 A2 | 6/2011 | |
| WO | 2011072084 A2 | 6/2011 | |
| WO | 2011106735 A1 | 9/2011 | |
| WO | 2011109813 A2 | 9/2011 | |
| WO | 2011159342 A1 | 12/2011 | |
| WO | 2011163275 A2 | 12/2011 | |
| WO | 2012027487 A2 | 3/2012 | |
| WO | 2012036742 A2 | 3/2012 | |
| WO | 2012095116 A1 | 7/2012 | |
| WO | 2012177942 A2 | 12/2012 | |
| WO | 2013028387 A2 | 2/2013 | |
| WO | 2013045262 A1 | 4/2013 | |
| WO | 2013059747 A1 | 4/2013 | |
| WO | 2013096411 A1 | 6/2013 | |
| WO | 2013175468 A2 | 11/2013 | |
| WO | 2014071077 A1 | 5/2014 | |
| WO | 2014121280 A2 | 8/2014 | |
| WO | 2014144937 A2 | 9/2014 | |
| WO | 2014162306 A2 | 10/2014 | |
| WO | 2014189974 A1 | 11/2014 | |
| WO | 2015051430 A1 | 4/2015 | |
| WO | 2015058039 A1 | 4/2015 | |
| WO | 2015063580 A2 | 5/2015 | |
| WO | 2015065646 A1 | 5/2015 | |
| WO | 2015120122 A2 | 8/2015 | |
| WO | 2015138306 A2 | 9/2015 | |
| WO | 2015173706 A1 | 11/2015 | |
| WO | 2016112085 A2 | 7/2016 | |
| WO | 2016126942 A2 | 8/2016 | |
| WO | 2016168609 A1 | 10/2016 | |
| WO | 2016196933 A1 | 12/2016 | |
| WO | 2017096157 A1 | 6/2017 | |
| WO | 2017132008 A1 | 8/2017 | |
| WO | 2017218375 A1 | 12/2017 | |
| WO | 2018005779 A1 | 1/2018 | |
| WO | 2018013515 A1 | 1/2018 | |
| WO | 2019144121 A1 | 7/2019 | |

OTHER PUBLICATIONS

Dale, Theodore, et al., U.S. Appl. No. 17/112,169, filed Dec. 4, 2020, Titled "Braided Anchor For Mitral Valve".
Robert C. Ashton Jr., "Development of an Intraluminal Device for the Treatment of Aortic Regurgitation: Prototype and In Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vasc Interv Radiol., Jul. 2003, 4:841-853.
Ross, D. N., "Aortic Valve Surgery," Guys Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Search Report for CN201680033815.7 dated Nov. 1, 2019, 3 pages.
Second Office Action for Chinese Application No. 201480037269.5, dated Nov. 6, 2017, 6 pages.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Third Office Action for Chinese Application No. 201480037269.5, dated Jun. 19, 2018, 8 pages.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
US 9,155,620, Oct. 2015, Gross et al. (withdrawn)
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http:/webdocs.cs.ualberta.ca/~database/MEMS/sma.html>, Feb. 5, 2016, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Australian Examination Report for Application No. 2016248314 dated Oct. 4, 2019, pp. 1-5.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive Cardiovascular and Thoracic Surgery, 2005, 4:475-477.

(56) References Cited

OTHER PUBLICATIONS

Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Examination Report for European Application No. 14734333.9, dated Oct. 20, 2016, 6 pages.
Examination Report No. 1 for Australian Application No. 2014274056, dated Mar. 6, 2018, 4 pages.
Examination Report No. 2 for Australian Application No. 2014274056, dated May 9, 2018, 2 pages.
Extended European Search Report for European Application No. 18160595.7, dated Sep. 14, 2018, 7 pages.
Extended European Search Report including Written Opinion for Application No. EP20168419.8, dated Jul. 21, 2020, pp. 1-8.
Extended European Search Report including Written Opinion for EP20211930.1 dated Apr. 28, 2021; 8 pages.
Extended European Search Report issued in Appln. No. 21165656.6 dated Aug. 11, 2021 (2 pages).
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http:/education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2014/040188, dated Nov. 17, 2014, 12 pages.
Invitation to Pay Additional Fees and Partial International Search Report for International Application No. PCT/US2014/040188, dated Sep. 8, 2014, 5 pages.
Japanese Office Action for Application No. 2020105100, dated Jun. 4, 2021, 4 pages.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991, retrieved from the Internet on Feb. 5, 2016, 3 pages.
L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./ Oct. 1996, 42(5):M381-M385.
Notice of Reasons for Rejection for Japanese Application No. 2016-517032, dated Feb. 13, 2018, 5 pages.
Office Action for Chinese Application No. 201480037269.5, dated Dec. 23, 2016.
Office Action for U.S. Appl. No. 14/950,656, dated Apr. 22, 2016, 5 pages.
Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.

\* cited by examiner

APPARATUS AND METHODS FOR VALVE AND TETHER FIXATION

CROSS-REFERENCE TO RELATED APPLICATIONS

The present application claims the benefit of the filing date of U.S. Provisional Patent Application No. 63/001,637 filed Mar. 30, 2020, the disclosure of which is hereby incorporated by reference.

BACKGROUND

Valvular heart disease, and specifically aortic and mitral valve disease, is a significant health issue in the United States. Valve replacement is one option for treating heart valves diseases. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated with the procedure, largely due to the necessity for extra-corporeal circulation. Further, open heart surgery is often poorly tolerated in elderly patients. Thus, if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated with the native mitral valve and thus a greater level of difficulty with regard to inserting and anchoring the replacement prosthesis.

Recent developments in the field have provided devices and methods for mitral valve replacement with reduced invasion and risk to the patient. Such devices may include a prosthetic valve disposed within the native valve annulus and held in place with an anchor seated against an exterior surface of the heart near the ventricular apex, and such anchors must be at least a certain size to seat against the heart with adequate security. Methods of implanting such devices therefore typically require providing an intercostal puncture of significant size to accommodate the anchor. Trauma to the patient increases as a function of the diameter of the puncture. Accordingly, methods and devices for anchoring a prosthetic heart valve that avoid the need for an intercostal puncture would improve patient outcomes.

BRIEF SUMMARY

According to a first aspect of the disclosure, a prosthetic heart valve system includes a prosthetic heart valve, an anchor and a tether. The prosthetic heart valve may have an expandable stent and a prosthetic valve assembly disposed within the stent. The prosthetic heart valve may have a prosthetic valve assembly configured to allow blood to flow in a direction from an inflow end of the stent toward an outflow end of the stent and to substantially block blood from flowing from the outflow end of the stent toward the inflow end of the stent. The prosthetic heart valve may include a tether connecting portion. The anchor may be adapted to be disposed on or adjacent an epicardial surface of a heart of a patient. The tether may have a distal end coupled to the anchor and extend proximally from the anchor. The tether may define a protrusion having a width greater than portions of the tether adjacent the protrusion. The prosthetic heart valve may be configured to translate along the tether toward the distal end of the tether, and the protrusion of the tether may be configured to engage the tether connecting portion to prevent proximal movement of the prosthetic heart valve relative to the tether.

According to another embodiment of the disclosure, a prosthetic heart valve system includes a prosthetic heart valve, an anchor and a tether. The prosthetic heart valve may have an expandable stent and a prosthetic valve assembly disposed within the stent. The prosthetic valve assembly may be configured to allow blood to flow in a direction from an inflow end of the stent toward an outflow end of the stent and to substantially block blood from flowing from the outflow end of the stent toward the inflow end of the stent. The prosthetic heart valve may include a tether connecting portion. The anchor may be adapted to be disposed on or adjacent an epicardial surface of a heart of a patient. The tether may have a distal end coupled to the anchor and extend proximally from the anchor. The tether connecting portion may include a stem having a radially expanded condition, a radially collapsed condition, and a barb extending radially inward from the stem. The barb may be configured to pierce the tether upon transition of the stem from the radially expanded condition to the radially collapsed condition.

According to another embodiment of the disclosure, a prosthetic heart valve system includes a prosthetic heart valve, an anchor, a tether clip and a tether. The prosthetic heart valve may have an expandable stent and a prosthetic valve assembly disposed within the stent. The prosthetic valve assembly may be configured to allow blood to flow in a direction from an inflow end of the stent toward an outflow end of the stent and to substantially block blood from flowing from the outflow end of the stent toward the inflow end of the stent. The prosthetic heart valve may include a tether connecting portion. The anchor may be adapted to be disposed on or adjacent an epicardial surface of a heart of a patient. The tether may have a distal end coupled to the tether clip, a proximal end coupled to the tether connecting portion, a first intermediate tether portion looped around the anchor, and a second intermediate tether portion. The second intermediate tether portion may be threaded through an aperture in the tether clip, and the tether clip may be configured to slide along the second intermediate tether portion to adjust a tension of the tether.

According to another embodiment of the disclosure, a method of implanting a prosthetic heart valve includes positioning an anchor adjacent a ventricular wall while a tether is coupled to and extends proximally from the anchor. The prosthetic heart valve may be advanced distally along the tether while the anchor is positioned adjacent the ventricular wall. The prosthetic heart valve may be deployed into a native valve annulus. The tether may be pulled in a proximal direction to tension the tether. The prosthetic heart valve may be fixed to the tether while the tether is tensioned.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. Further, the term "inflow end" when used herein in connection with a prosthetic atrioventricular valve refers to the end of the prosthetic valve nearest the atrium when the prosthetic valve is implanted in an intended position and orientation, while the term "outflow end" refers to the end of the prosthetic valve nearest the ventricle when the prosthetic valve is implanted in the intended position and orientation. As used herein, the terms "substantially," "generally," "approximately," and "about" are intended to mean that slight deviations from absolute are included within the scope of the term so modified.

Figure 1:
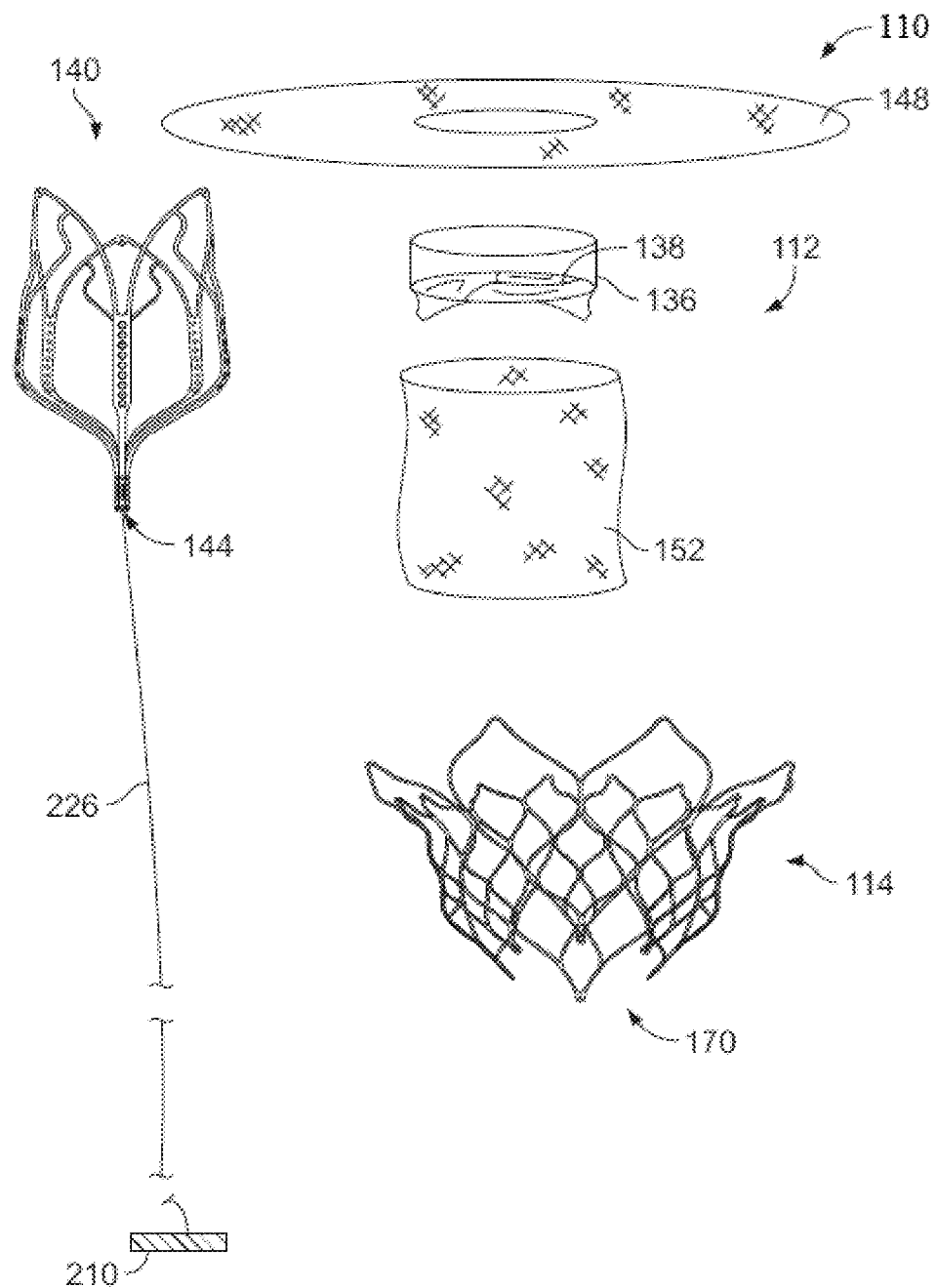
FIG. 1 is an exploded view of a prosthetic heart valve.

An exemplary prosthetic heart valve 110 as may be used with various embodiments of the present disclosure is shown in an exploded view in FIG. 1. Valve 110 includes an inner structure or assembly 112 and an outer structure or assembly 114. Valve 110 may be coupled to a tether 226 and a collapsible tether anchor 210.

Inner assembly 112 may include an inner frame 140, outer wrap 152 which may be cylindrical, and leaflet structure 136 (including articulating leaflets 138 that define a valve function). Leaflet structure 136 may be sewn to inner frame 140, and may use parts of inner frame 140 for this purpose, although methods of attachment other than sutures may be suitable. Inner assembly 112 is disposed and secured within outer assembly 114, as described in more detail below.

Outer assembly 114 includes outer frame 170. Outer frame 170 may also have in various embodiments an outer frame cover of tissue or fabric (not pictured), or may be left without an outer cover to provide exposed wireframe to facilitate in-growth of tissue. Outer frame 170 may also have an articulating collar or cuff (not pictured) covered by a cover 148 of tissue or fabric.

Tether 226 is connected to valve 110 by inner frame 140. Thus, inner frame 140 includes tether connecting or clamping portion 144 by which inner frame 140, and by extension valve 110, is coupled to tether 226.

Figure 2:
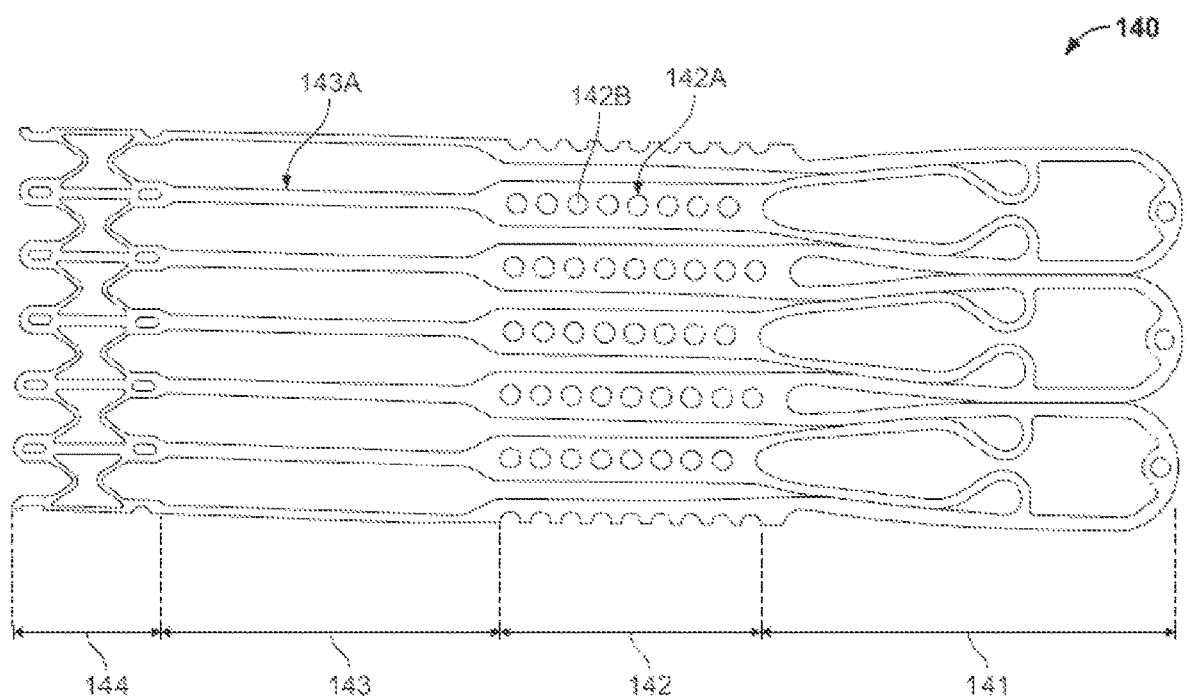
FIG. 2 is an opened and flattened view of an unexpanded inner frame of the prosthetic heart valve of FIG. 1.
Figure 3:
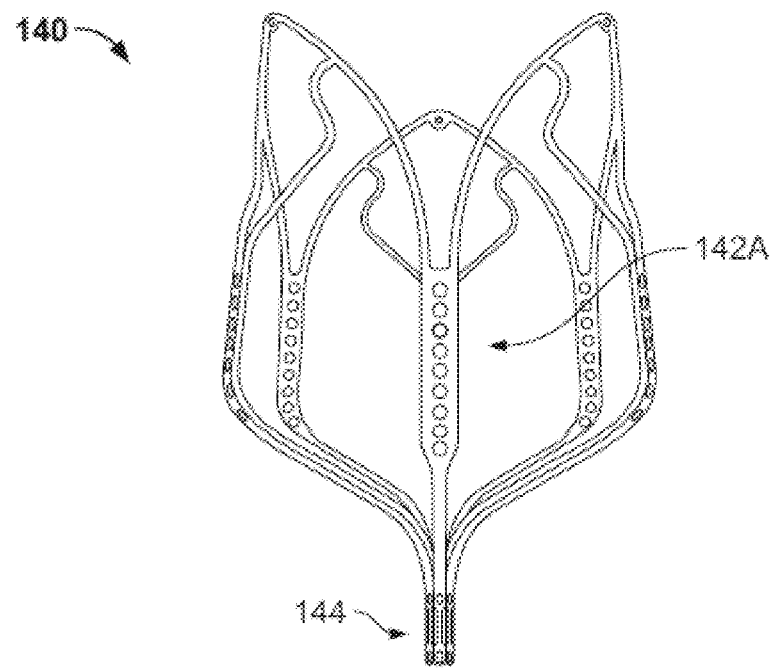
FIGS. 3 and 4 are side and bottom views, respectively, of the inner frame of FIG. 2 in an expanded configuration.
Figure 4:
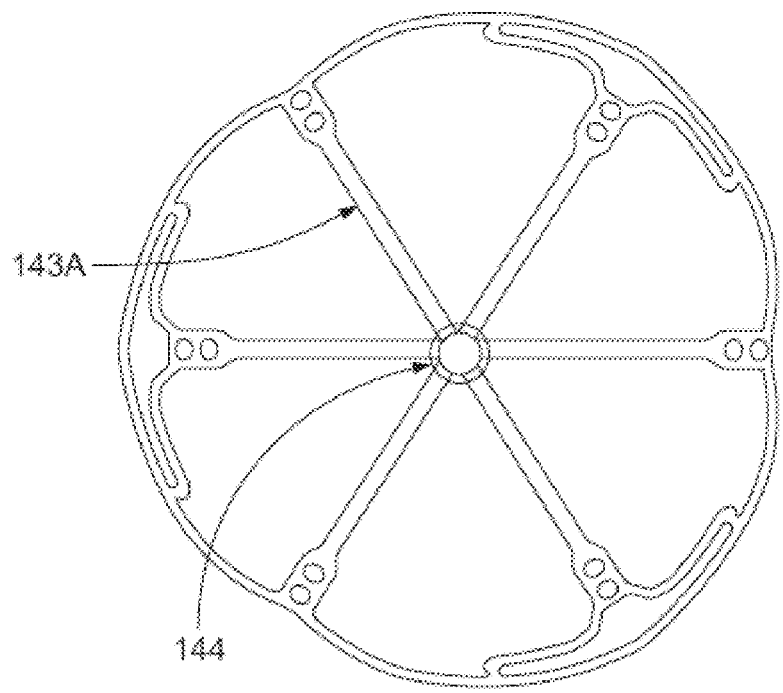

Inner frame 140 is shown in more detail in FIGS. 2-4. Inner frame 140 can be formed from a milled or laser-cut tube of a shape-memory material such as, for example, nitinol. Inner frame 140 is illustrated in FIG. 2 in an initial state, e.g., as milled or laser-cut, but cut longitudinally and unrolled into a flat sheet for ease of illustration. This initial state may generally correspond to a collapsed condition. Inner frame 140 is shown unconstrained, e.g., to the expanded, deployed configuration, in the side view and bottom view of FIGS. 3 and 4, respectively. Inner frame 140 can be divided into four portions corresponding to functionally different portions of inner frame 140 in final form: apex portion 141, body portion 142, strut portion 143, and tether connecting portion 144. Strut portion 143 includes six struts, such as strut 143A, which connect body portion 142 to connecting portion 144. A greater or fewer number of struts 143A is contemplated herein.

Connecting portion 144 includes longitudinal extensions of the struts 143A, connected circumferentially to one another by pairs of v-shaped connecting members, which may be referred to herein as "micro-V's." Connecting portion 144 is configured to be radially collapsed by application of a compressive force, which causes the micro-V's to become more deeply V-shaped, with each pair of vertices moving closer together longitudinally and the open ends of the V shapes moving closer together circumferentially. When collapsed, connecting portion 144 can clamp or grip one end of tether 226, either connecting directly onto a tether line (e.g., braided filament line) or onto an intermediate structure, such as a polymer or metal piece that is, in turn, firmly fixed to the tether line. The foregoing is merely exemplary and other techniques can be used to connect tether 226 to connecting portion 144, as will be discussed below in further detail.

In contrast to connecting portion 144, apex portion 141 and body portion 142 are configured to be expanded radially. Strut portion 143 forms a longitudinal connection, and radial transition, between the expanded body portion 142 and the compressed connecting portion 144.

Body portion 142 includes six longitudinal posts, such as post 142A, although the body portion may include a greater or fewer number of such posts. The posts 142A can be used to attach leaflet structure 136 to inner frame 140, and/or can be used to attach inner assembly 112 to outer assembly 114, such as by connecting inner frame 140 to outer frame 170. In the illustrated example, posts 142A include apertures 142B through which connecting members (such as suture filaments and/or wires) can be passed to couple the posts to other structures.

Figure 5:
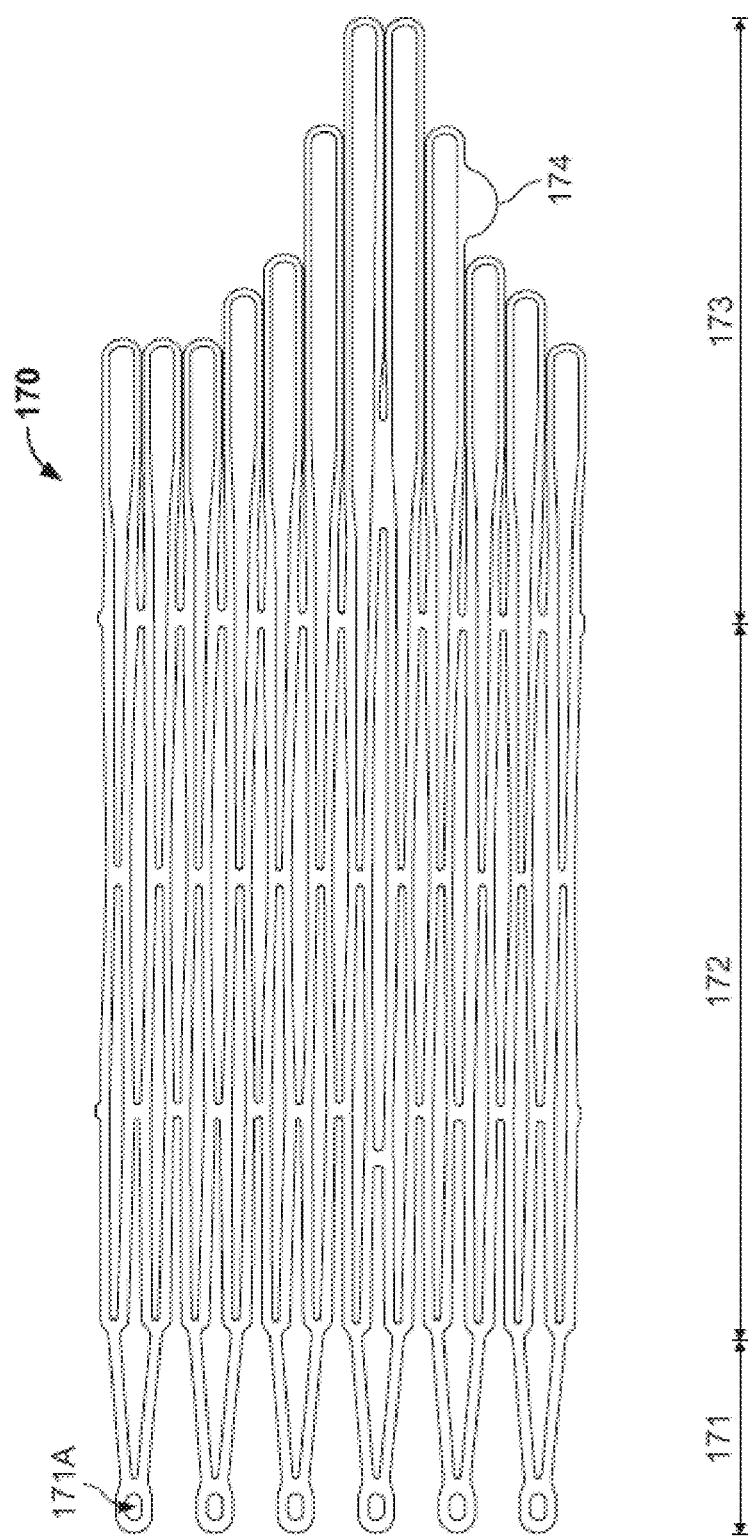
FIG. 5 is an opened and flattened view of an unexpanded outer frame of the prosthetic heart valve of FIG. 1.
Figure 6:
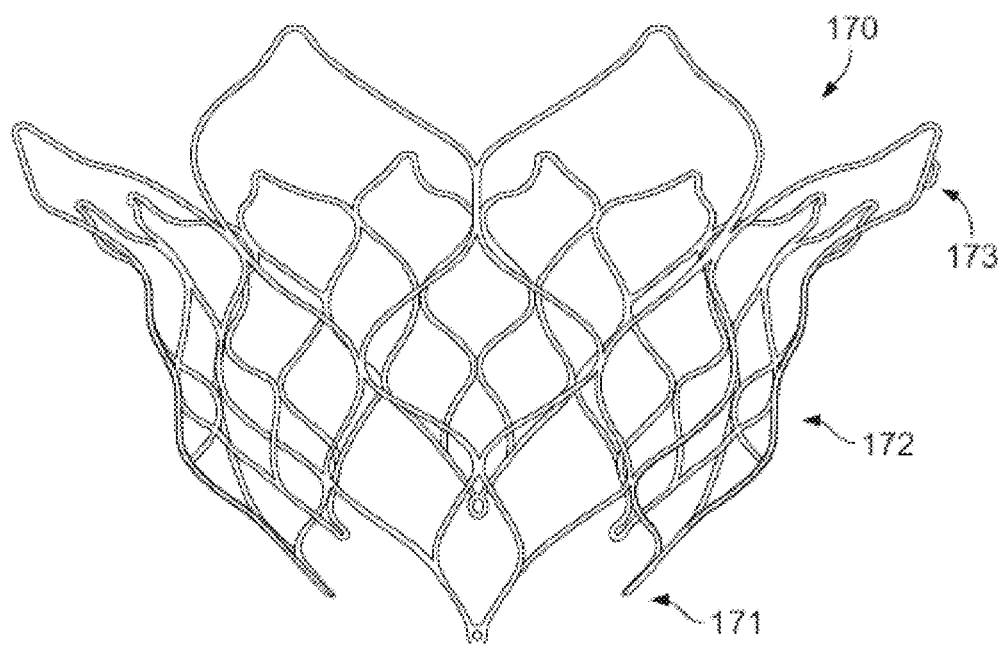
FIGS. 6 and 7 are side and top views, respectively, of the outer frame of FIG. 5 in an expanded configuration.
Figure 7:
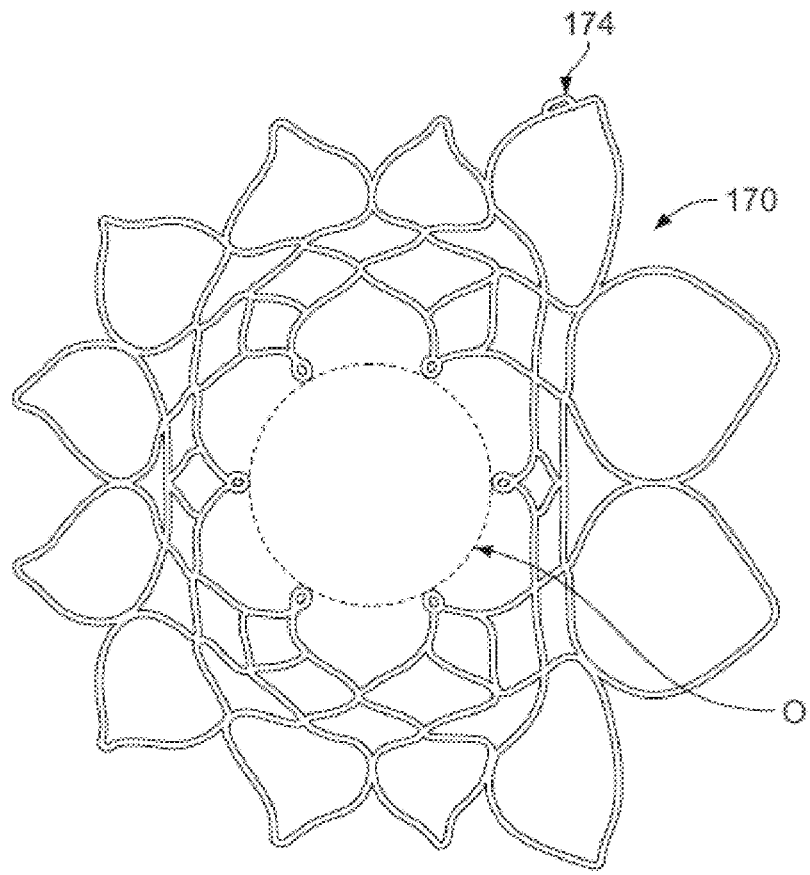

Outer frame 170 of valve 110 is shown in more detail in FIGS. 5-7. Outer frame 170 can be formed from a milled or laser-cut tube of a shape-memory material such as, for example, nitinol. Outer frame 170 is illustrated in FIG. 5 in an initial state, e.g., as milled or laser-cut, but cut longitudinally and unrolled into a flat sheet for ease of illustration. This initial state may generally correspond to the collapsed condition. Outer frame 170 can be divided into a coupling portion 171, a body portion 172, and a flared portion 173, as shown in FIG. 5. Coupling portion 171 may include multiple openings or apertures 171A by which outer frame 170 can be coupled to inner frame 140, as described in greater detail below.

Flared portion 173 may include an indicator 174. In one example, indicator 174 is simply a broader portion of the wire frame element of flared portion 173. Indicator 174 may be more apparent in radiographic or other imaging modalities than the surrounding wireframe elements of flared portion 173. In other examples, indicator 174 can be any distinguishable feature (e.g., protrusion, notch, etc.) and/or indicia (e.g., lines, markings, tic marks, etc.) that enhance the visibility of the part of flared portion 173 on which it is formed, or to which it is attached. Indicator 174 can facilitate the implantation of the prosthetic valve by providing a reference point or landmark that the operator can use to orient and/or position the valve (or any portion of the valve) with respect to the native valve annulus or other heart structure. For example, during implantation, an operator can identify (e.g., using echocardiography) indicator 174 when the valve 110 is situated in a patient's heart. The operator can therefore determine the location and/or orientation of the valve and make adjustments accordingly.

Outer frame 170 is shown in an expanded, deployed configuration, in the side view and top view of FIGS. 6 and 7, respectively. As best seen in FIG. 7, the lower end of coupling portion 171 may form a roughly circular opening (identified by "O" in FIG. 7). The diameter of this opening preferably corresponds approximately to the diameter of body portion 142 of inner frame 140, when the inner frame is in the expanded condition, to facilitate the coupling together of these two components of valve 110.

Figure 8:
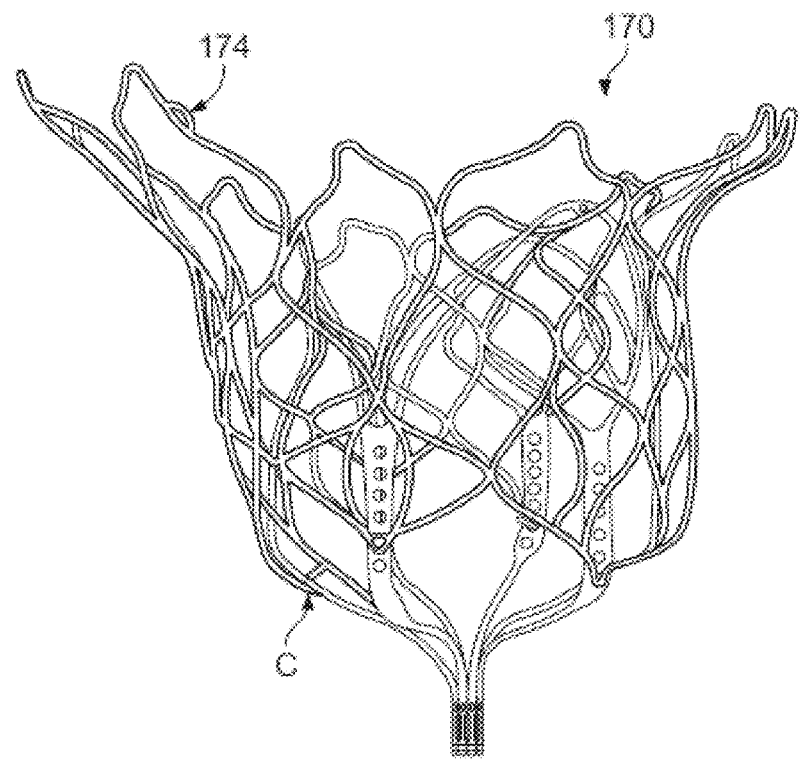
FIGS. 8-10 are side, front, and top views, respectively, of an assembly of the inner frame of FIGS. 2-4 and the outer frame of FIGS. 5-7, all in an expanded configuration.
Figure 9:
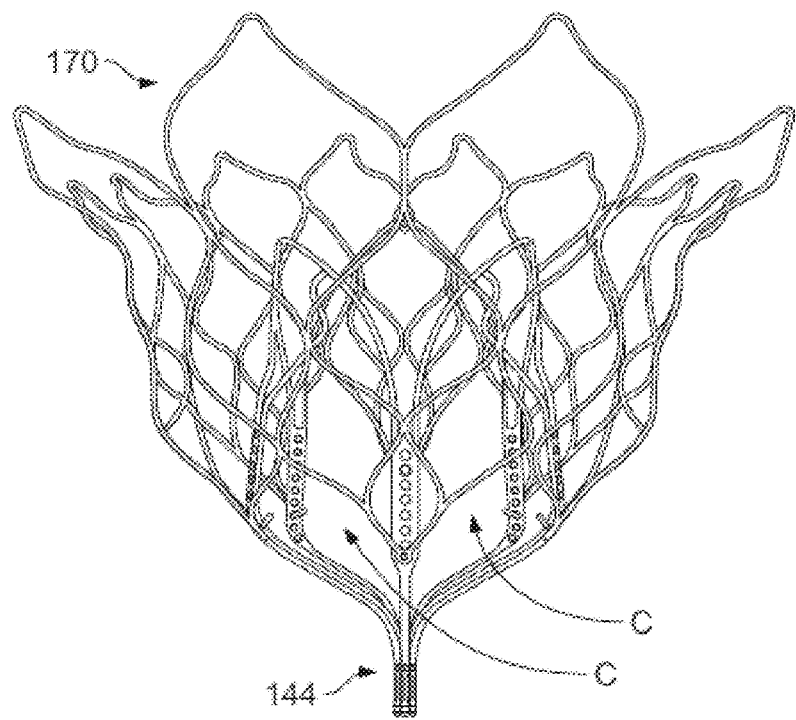
Figure 10:
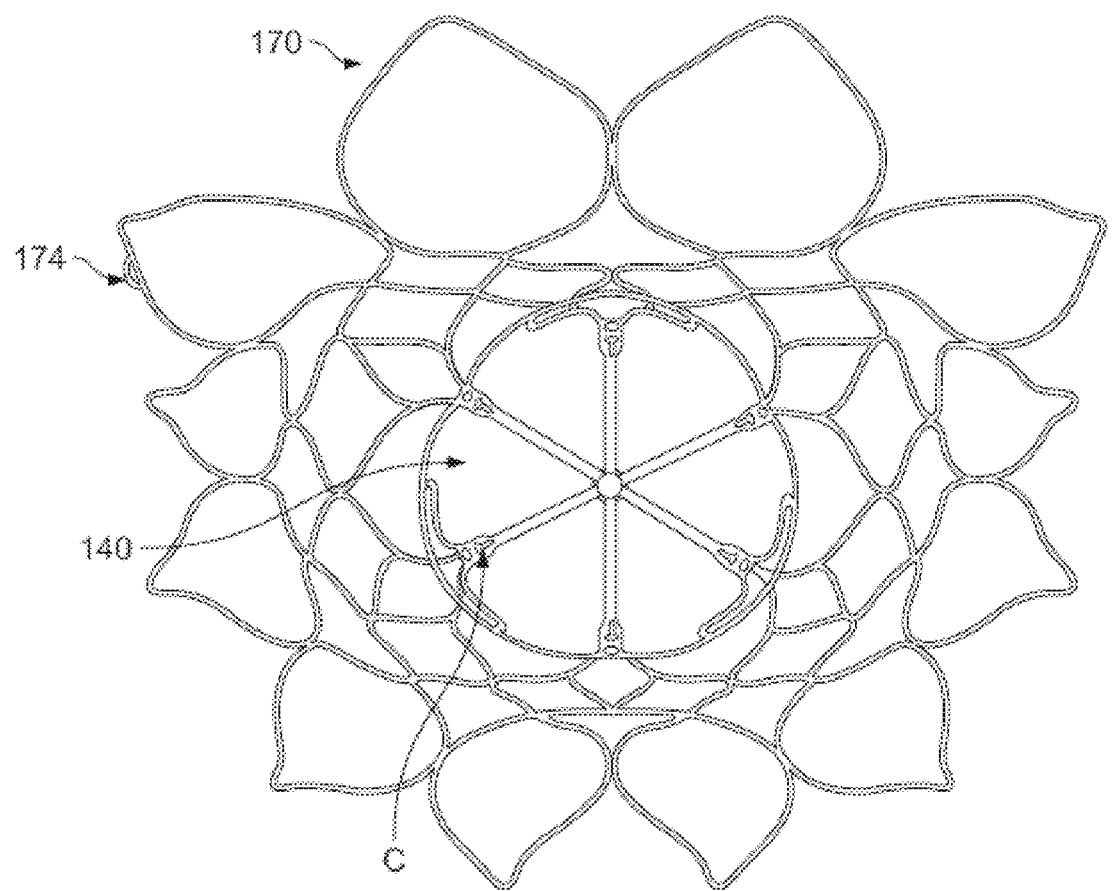

Outer frame 170 and inner frame 140 are shown coupled together in FIGS. 8-10 in front, side, and top views, respectively. The two frames collectively form a structural support for a valve leaflet structure, such as leaflet structure 136 in FIG. 1. The frames support leaflet structure 136 in the desired relationship to the native valve annulus, support the coverings for the two frames to provide a barrier to blood leakage between the atrium and ventricle, and couple to the tether 226 (by the inner frame 140) to aid in holding the prosthetic valve in place in the native valve annulus by the connection of the free end of the tether and tether anchor 210 to the ventricle wall, as described more fully below. The two frames are connected at six coupling points (representative points are identified as "C"). In this embodiment, the coupling of the frames is implemented with a mechanical fastener, such as a short length of wire, passed through an aperture 171A in coupling portion 171 of outer frame 170 and a corresponding aperture 142B in a longitudinal post 142A in body portion 142 of inner frame 140. Inner frame 140 is thus disposed within the outer frame 170 and securely coupled to it.

Figure 11A:
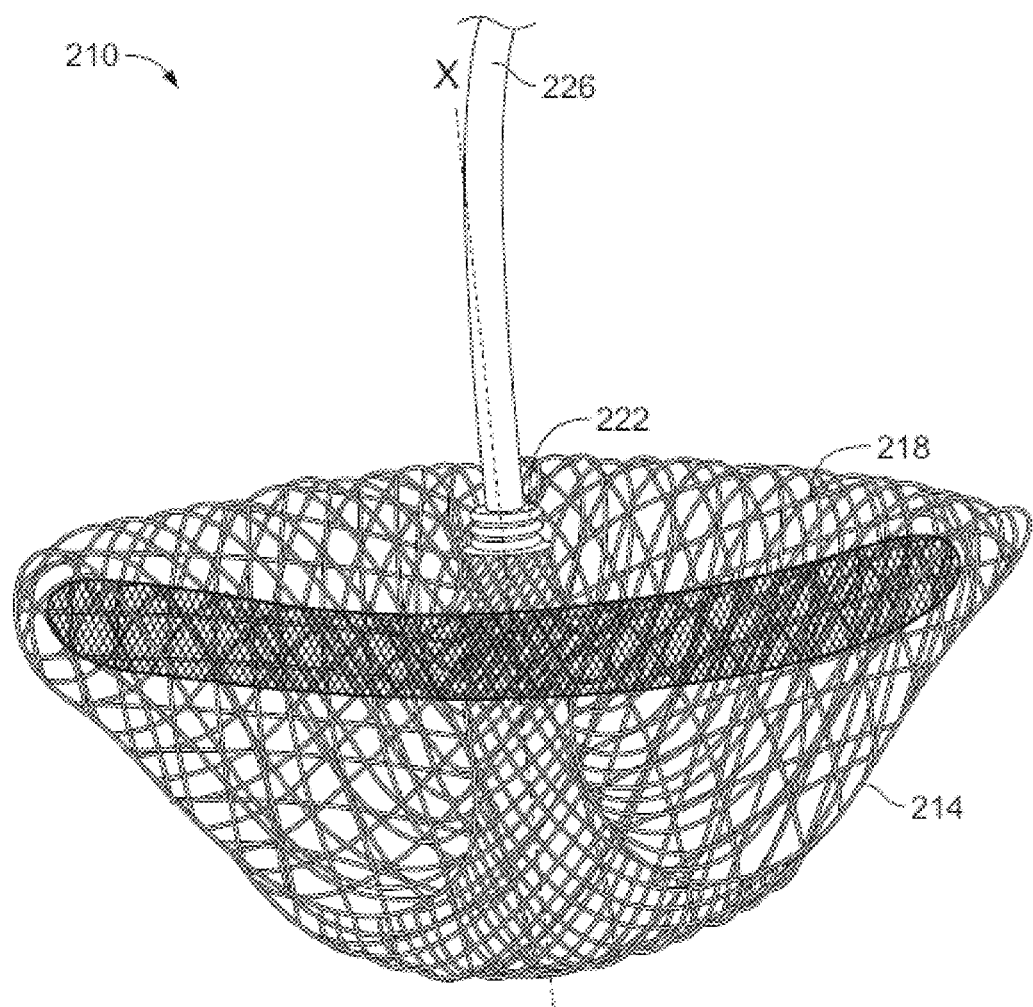
FIG. 11A is a perspective view of an anchor for the prosthetic valve of FIG. 1.
Figure 11B:
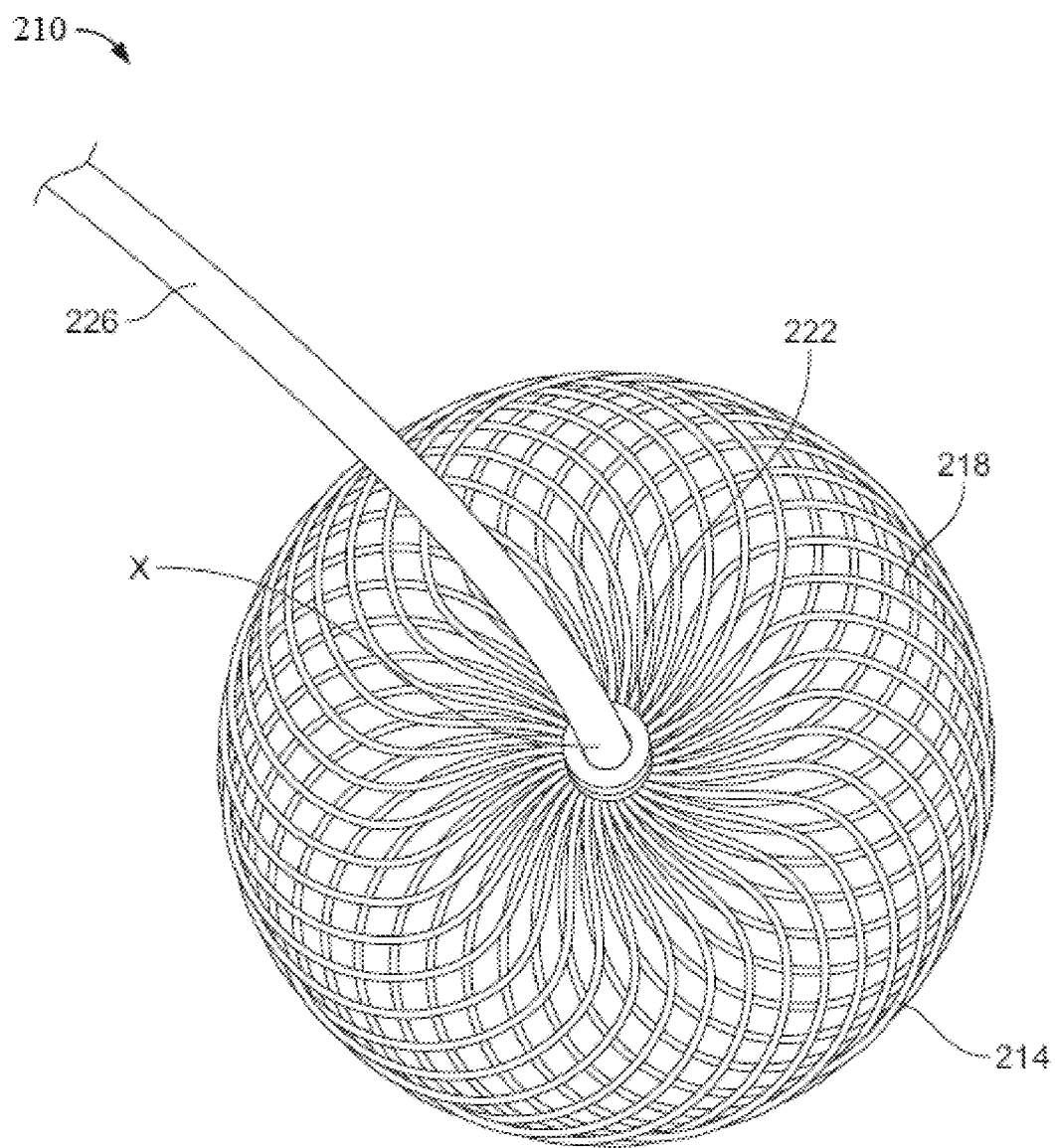
FIG. 11B is an axial view of the anchor of FIG. 11A.

An exemplary anchor 210 for a prosthetic mitral heart valve is illustrated in FIGS. 11A and 11B. Anchor 210 includes a first disc 214 and a second disc 218, both provided by a wire mesh and centered on an axis X. First disc 214 is offset from second disc 218 in a first direction along axis X. First disc 214 and second disc 218 are each biased toward a dome-shaped resting configuration that is concave toward a second direction along axis X, the second direction being opposite the first direction. The resting configuration of first disc 214 extends far enough in the second direction along axis X to partially overlap second disc 218.

Figure 12:
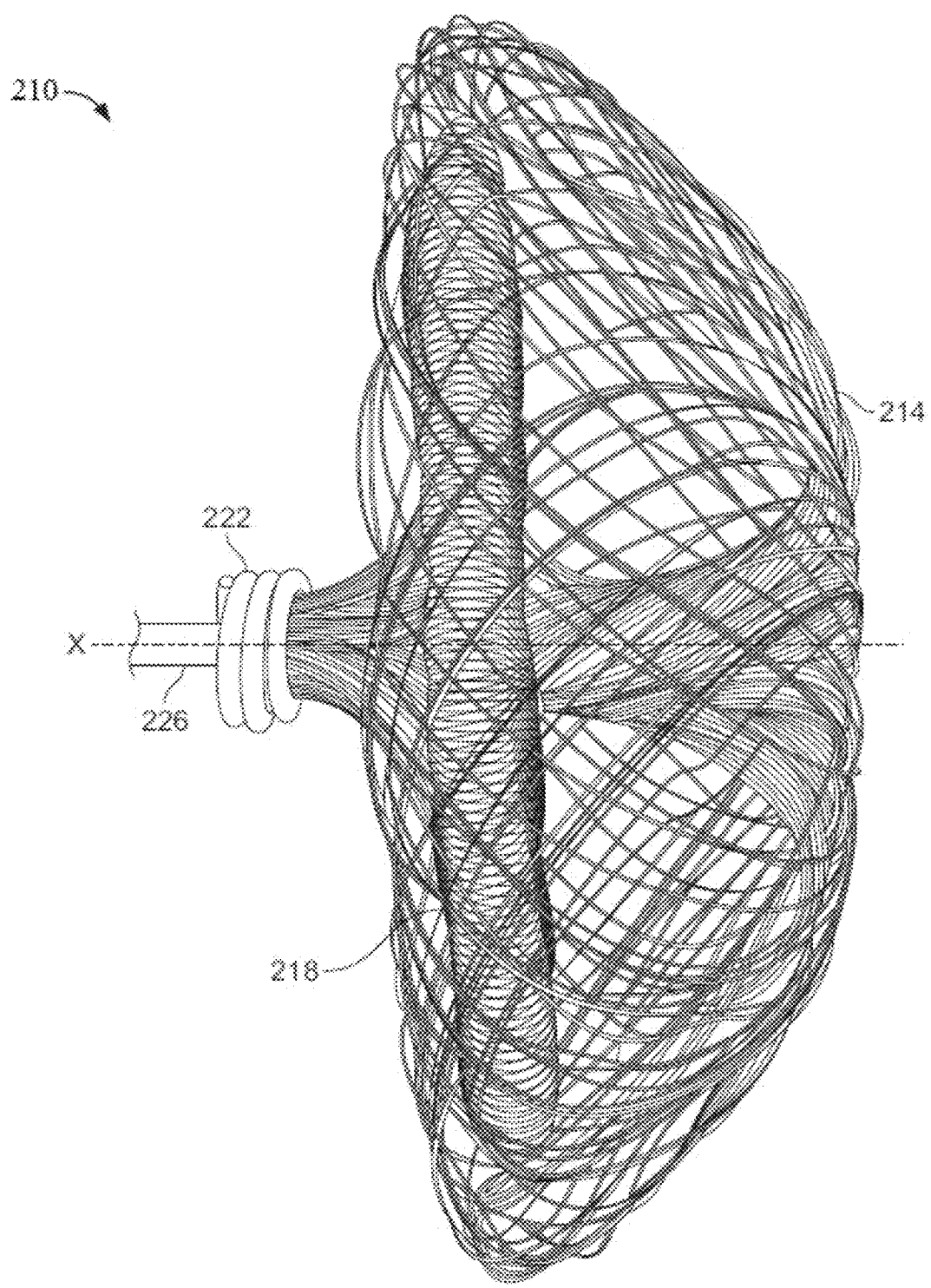
FIG. 12 is a side view of the anchor for the prosthetic valve of FIG. 1 according to another arrangement.

It should be understood that the illustrated dome shapes are merely exemplary, and first disc 214 and second disc 218 may be biased differently. For example, either or both of first disc 214 and second disc 218 may be biased toward a resting configuration that is convex toward the second direction or generally planar. Further, the first disc 214 and second disc 218 may be biased to different resting configurations. In one example, the first disc 214 may be biased toward a dome-shaped resting configuration that is concave toward the second direction while the second disc 218 is biased toward a generally planar configuration having about the same diameter location as the widest part of the dome-shaped resting configuration of the first disc 214, as shown in FIG. 12. In the arrangement shown in FIG. 12, second disc 218 is generally planar in shape with a shallow concavity toward the first direction near the center of second disc 218.

Anchor 210 may also include a cuff 222 for gripping a tether 226, which may be connected to a prosthetic heart valve. Cuff 222 is offset from second disc 218 in the second direction along axis X. One-way gripping features, such as angled teeth, within cuff 222 may permit anchor 210 to slide along tether 226 in the second direction, but not the first direction. In other embodiments, cuff 222 may be fixedly attached to tether 226 so that the anchor 210 may not slide along the tether.

Figure 13:
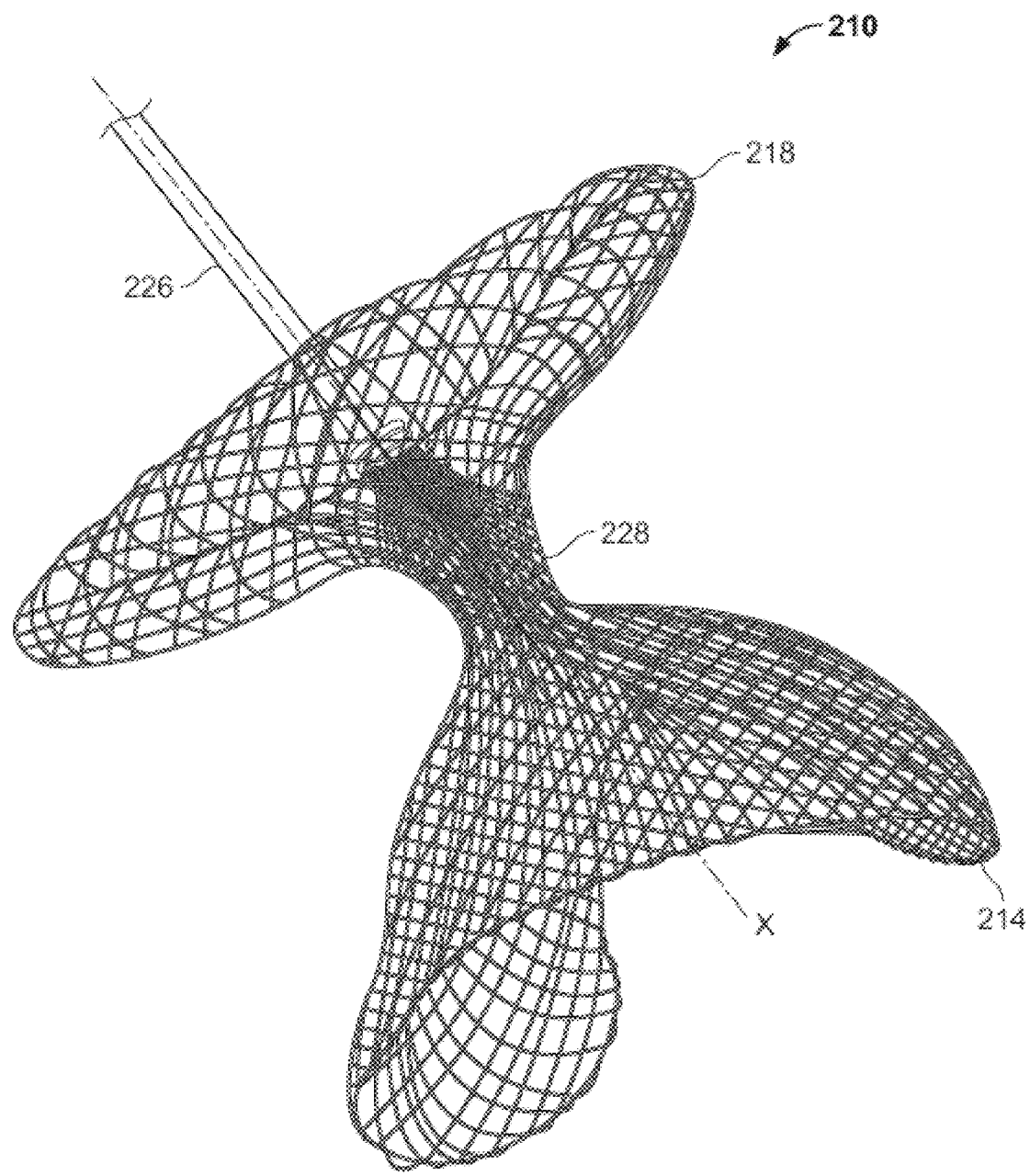
FIG. 13 is a perspective view of the anchor of FIG. 11 in a partially everted state.

Anchor 210 is flexible, as illustrated in FIG. 13, which shows anchor 210 with the first disc 214 everted from its resting configuration. First disc 214 is connected to second disc 218 by a neck 228 extending between first disc 214 and second disc 218. In the illustrated example, neck 228 is centered on axis X, but in other examples neck 228 may be radially offset from axis X. First disc 214, second disc 218, and neck 228 may all be constructed from a single continuous piece or tube of wire mesh. The wire mesh may be formed from a plurality of strands or wires braided into various three-dimensional shapes and/or geometries to engage tissues, or from one or more sheets cut to provide mesh, such as by laser. In one example, the wires form a braided metal fabric that is resilient, collapsible and capable of heat treatment to substantially set a desired shape. One class of materials which meets these qualifications is shape-memory alloys, such as nitinol. The wires may comprise various materials other than nitinol that have elastic and/or memory properties, such as spring stainless steel, trade-named alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of anchor 210. Shape memory materials such as nitinol may be particularly suitable for anchor 210 in that shape memory material construction enables anchor 210 to consistently return to an intended shape after being compressed and deployed. In other arrangements, anchor 210 may be covered by or may incorporate other flexible biocompatible material, such as a fabric. Although anchor 210 is one example of an expandable anchor that may be suitable for use with the prosthetic valves of the present disclosure, it should be understood that other anchors, including other expandable anchors, may also be suitable.

Figure 14:
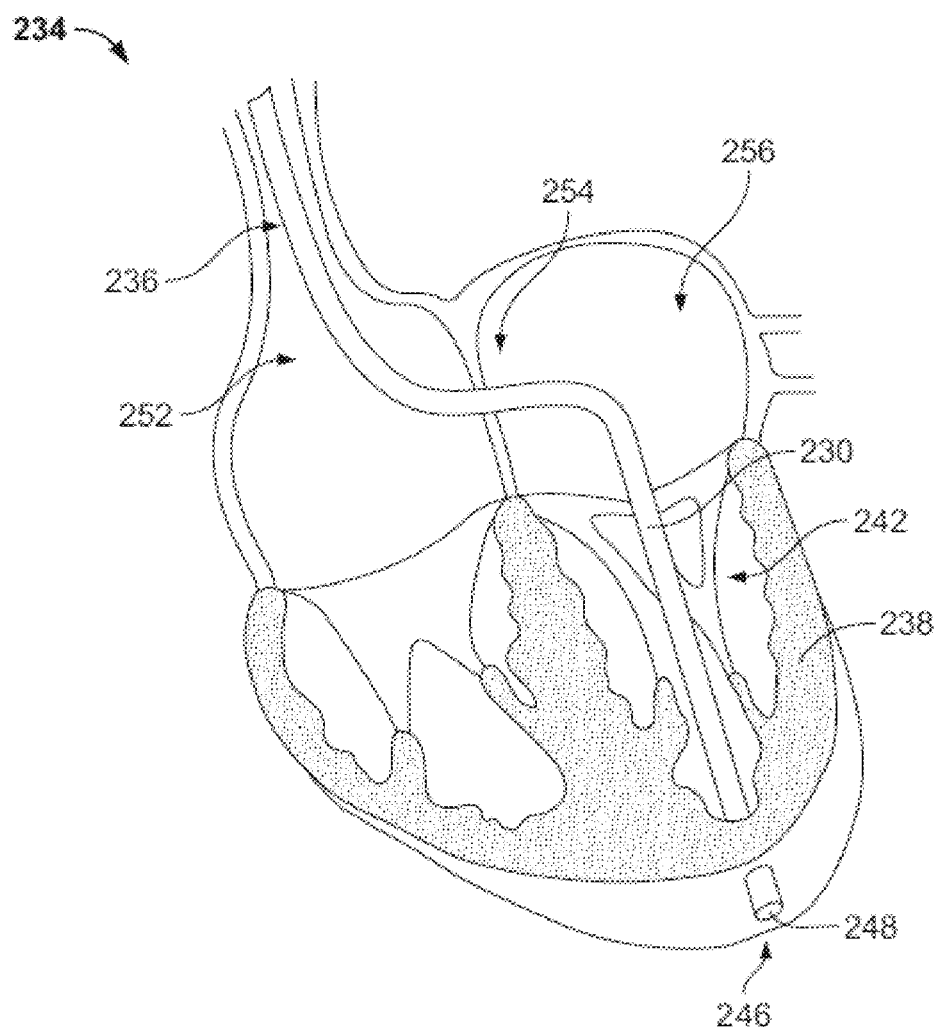
FIG. 14 illustrates a trans-jugular insertion of a delivery tube for the anchor of FIG. 11.

FIG. 14 shows a trans-jugular insertion of an at least partially flexible delivery tube 230 for anchor 210 and valve 110. Delivery tube 230 may be formed of any known material for building catheters, including biocompatible metals such as steel, and may be part of a steerable or flexible catheter system. Delivery tube 230 may include an inflexible portion near its distal end to facilitate the intended puncture of tissue and guidance of valve 110. Delivery tube 230 is inserted through the patient's jugular vein (not shown), then through superior vena cava 236, right atrium 252, atrial septum 254, left atrium 256, native mitral valve 260, and into left ventricle 242. Tube 230 exits left ventricle 242 through ventricular wall 238 at or near the apex 246 of heart 234. A retractable puncturing device (not shown) and a retractable atraumatic tip (not shown) may extend from the distal open end 248 of tube 230 in alternate stages of insertion of tube 230. The puncturing device may produce openings through atrial septum 254 and ventricular wall 238 while the atraumatic tip may act to prevent injury to other tissue. Once delivery tube 230 has been fully inserted, the distal open end 248 of tube 230 is positioned outside of ventricular wall 238. The trans-jugular insertion of tube 230 may be accomplished by any of variety of methods, such as, for example, guiding tube 230 along a guide wire, such as a shape-memory guide wire, inserted through the jugular vein. The flexible nature of anchor 210 allows trans-jugular delivery of anchor 210 through tube 230. Because tube 230, anchor 210, and valve 110 all reach heart 234 from the jugular vein, valve 110 and anchor 210 may be delivered and implanted without any intercostal puncture.

Figure 15:
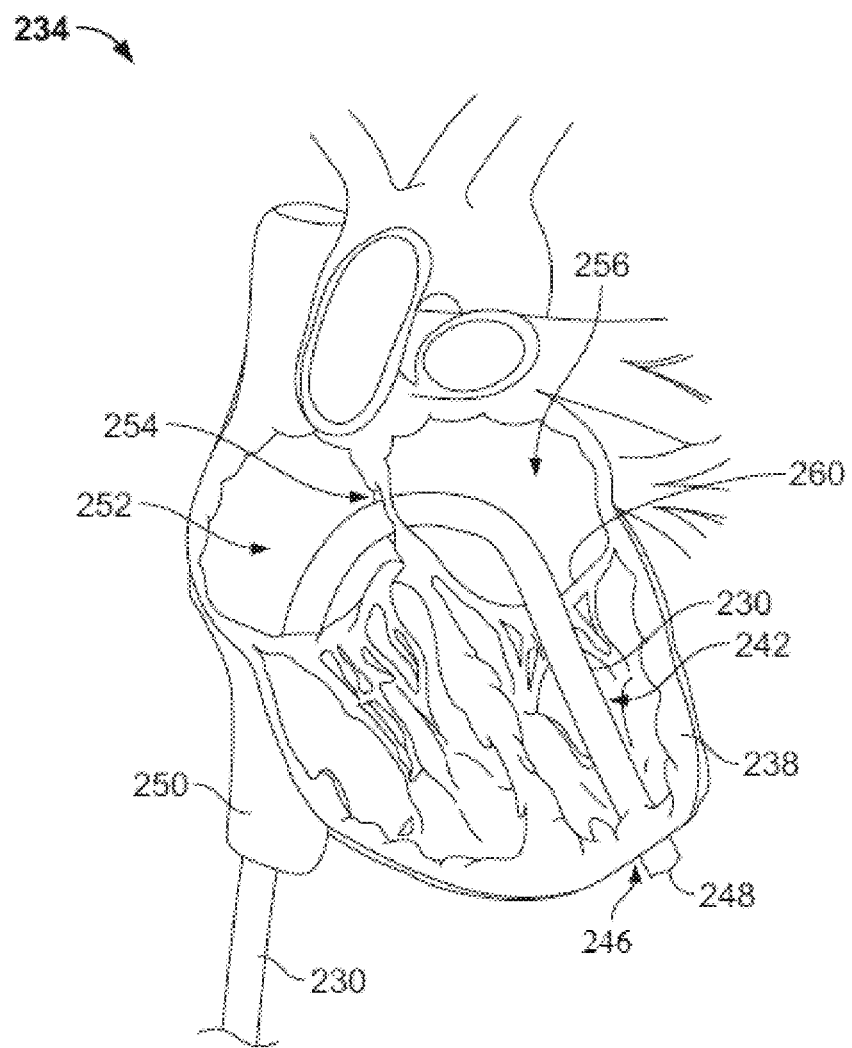
FIG. 15 illustrates a trans-femoral insertion of the delivery tube of FIG. 14.
Figure 16:
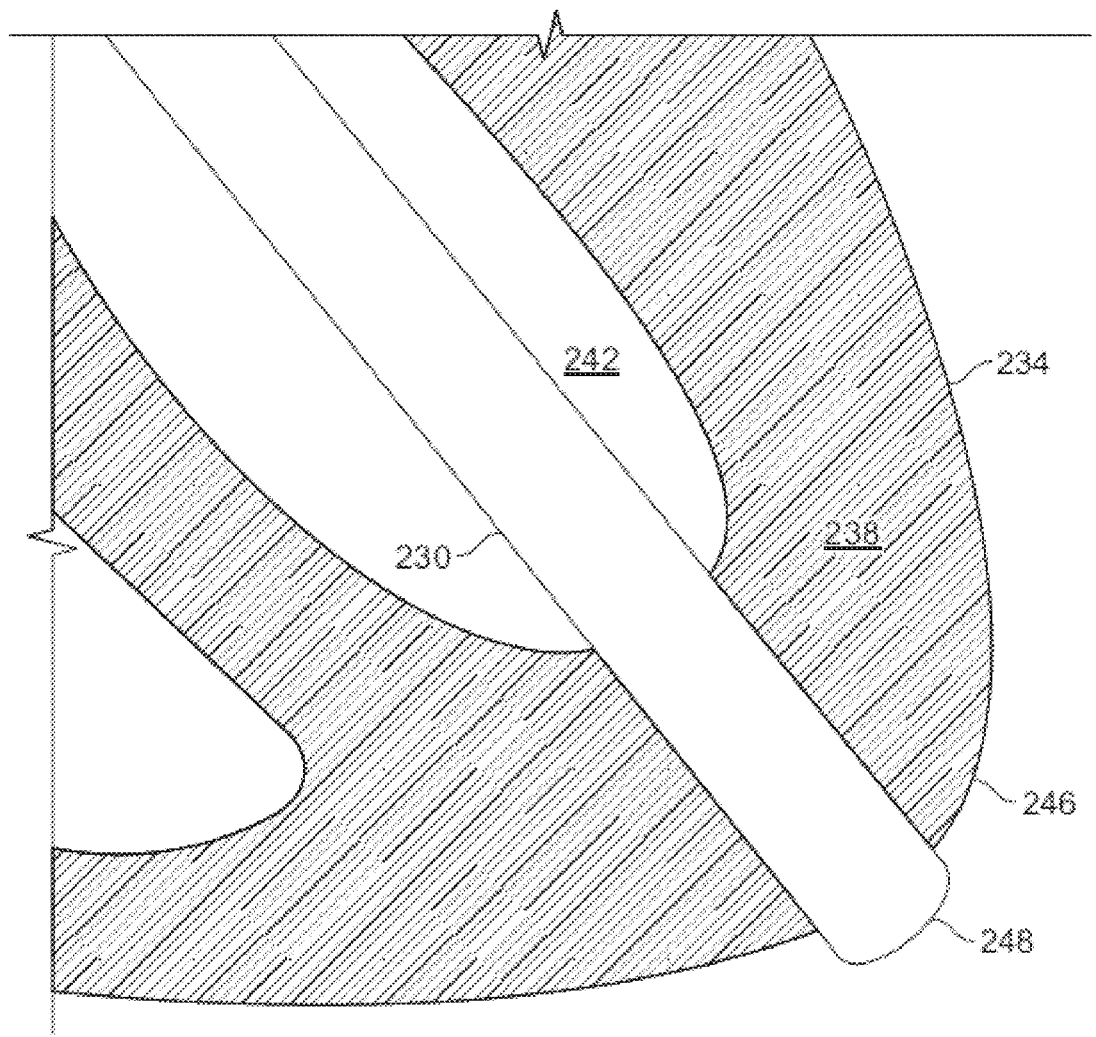
FIG. 16 illustrates the delivery tube of FIGS. 14 and 15 extending through a wall of a heart.

FIG. 15 shows a trans-femoral insertion of tube 230. Tube 230 enters heart 234 through inferior vena cava 250, travels through right atrium 252, and punctures septum 254 to enter left atrium 256. Tube 230 is advanced from left atrium 256 through native mitral valve 260, left ventricle 242, and ventricular wall 238 such that the open end 248 of the tube is positioned outside of wall 238 at or near apex 246. As with trans-jugular insertion, guidance of tube 230 during trans-femoral insertion may be accomplished using a variety of methods, including guidance along a guide wire.

The trans-jugular and trans-femoral insertions described above are merely exemplary. It should be understood that tube 230 could be guided toward heart 234 using any suitable method known in the art.

Figure 17:
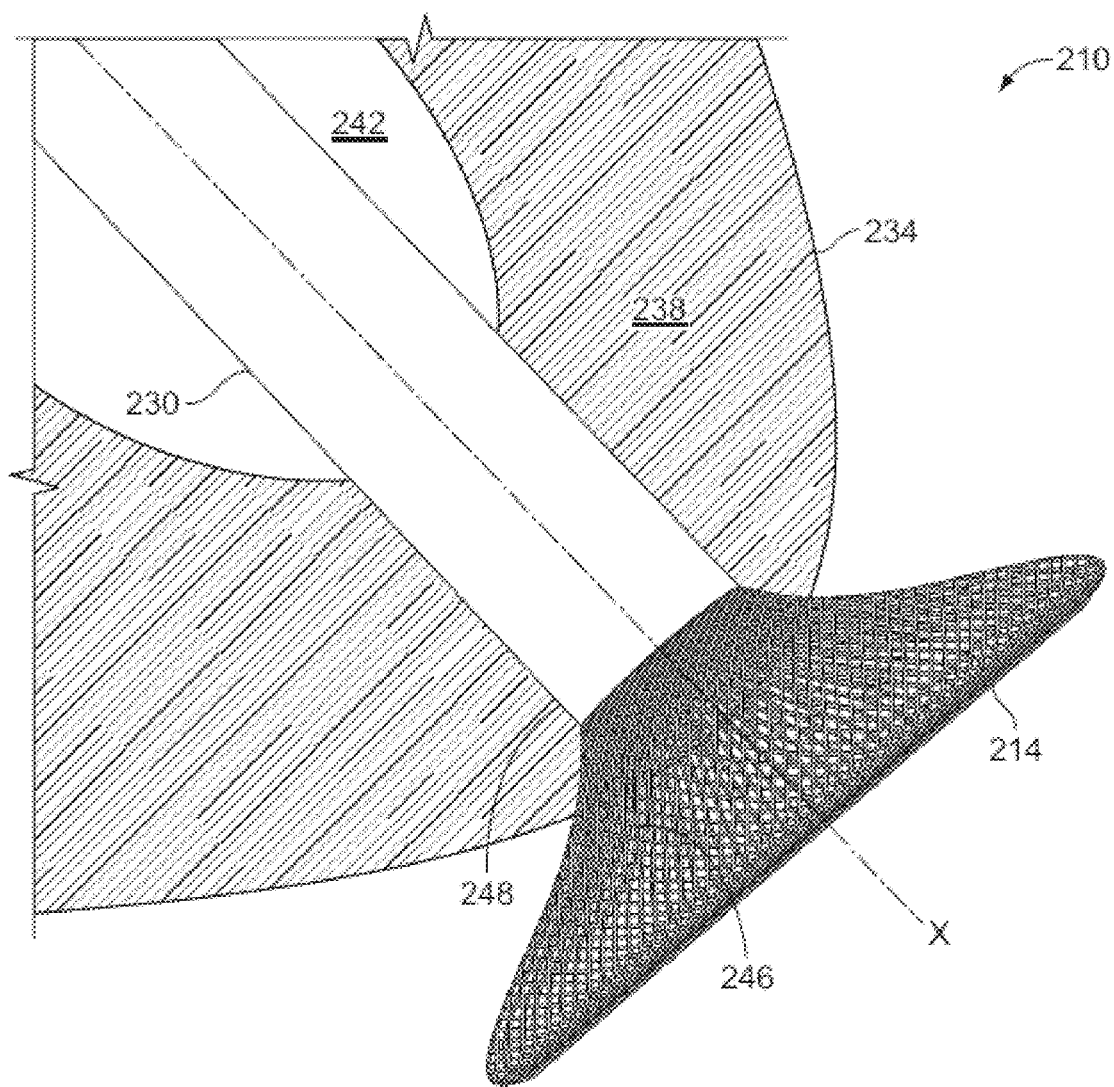
FIGS. 17-20 illustrate the anchor of FIG. 11 in progressive stages of deployment from the delivery tube of FIGS. 14 and 15.
Figure 18:
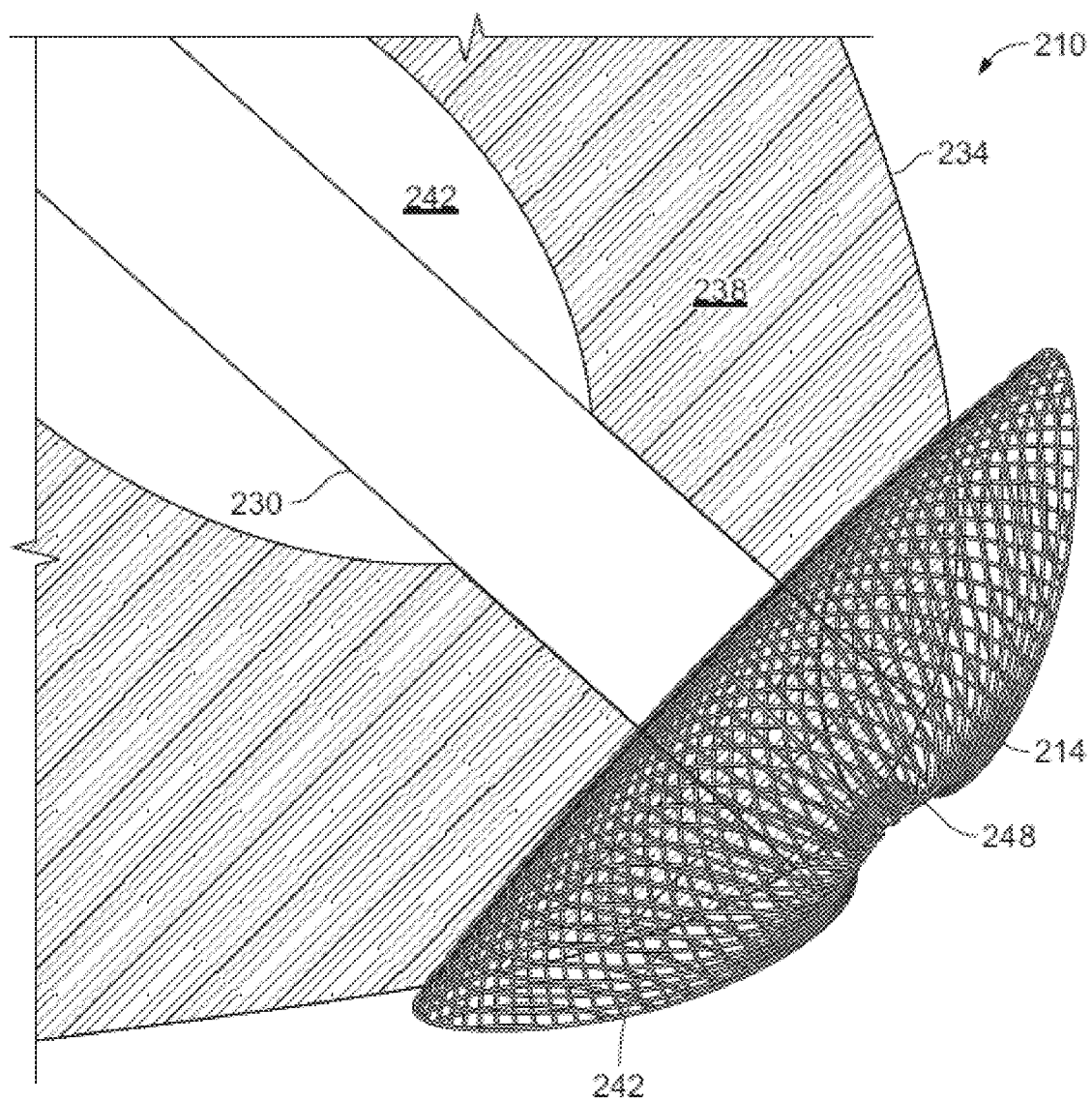
Figure 19:
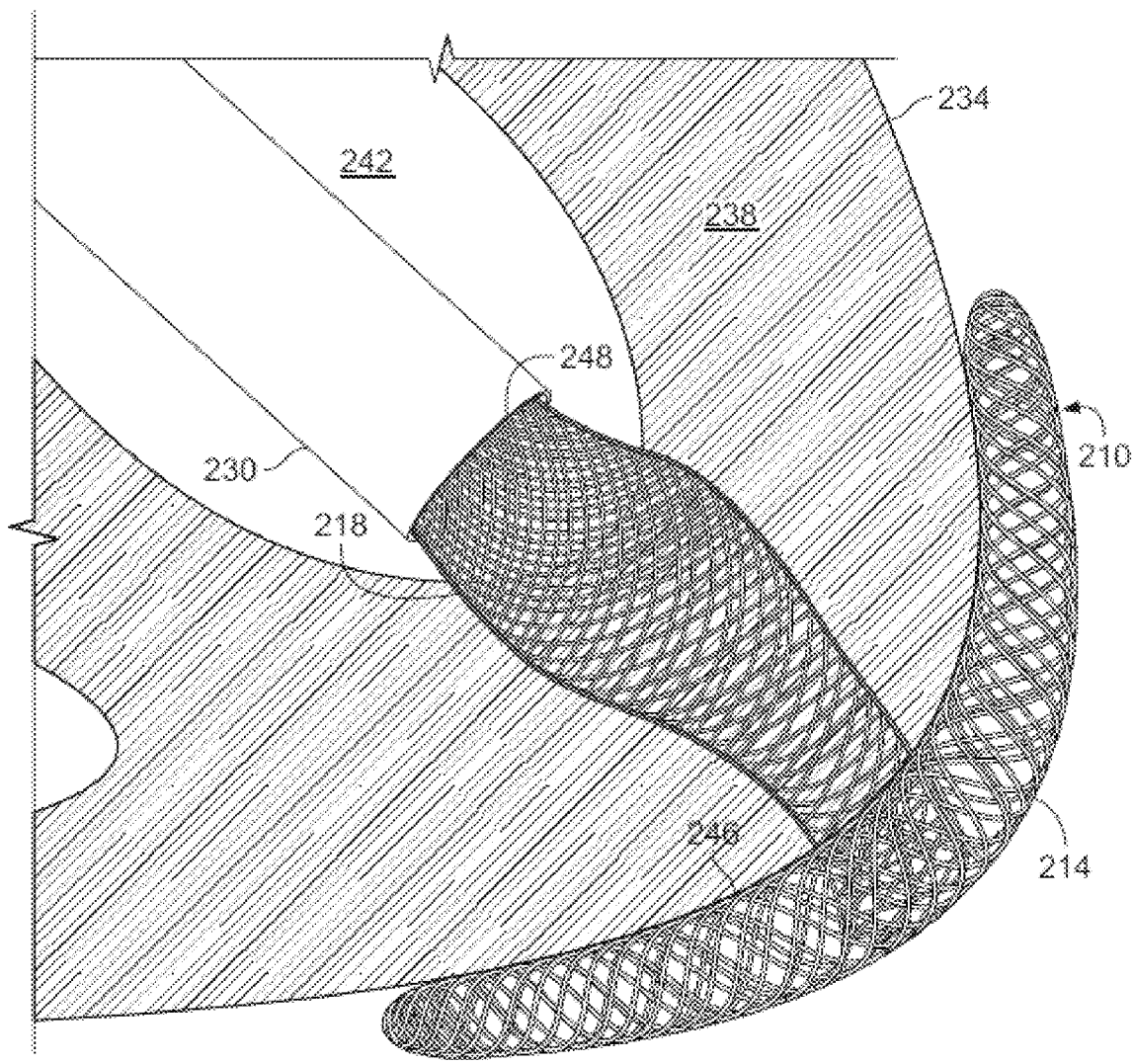
Figure 20:
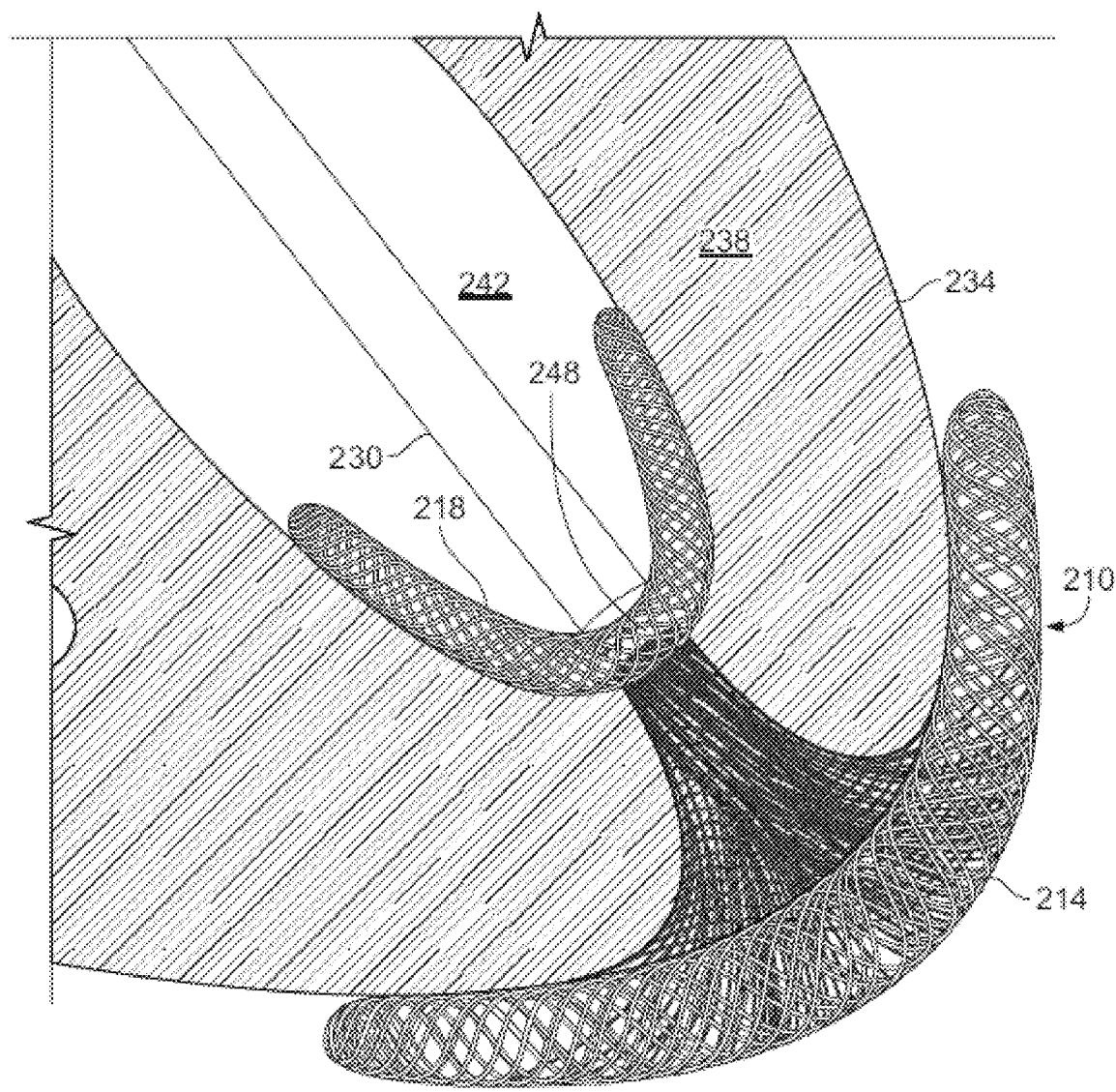
Figure 21A:
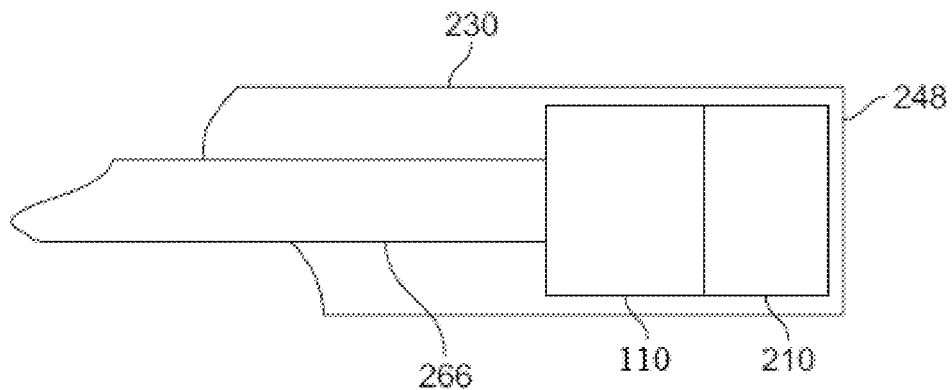
FIGS. 21A and 21B illustrate the delivery tube being retracted from the anchor of FIG. 11.
Figure 21B:
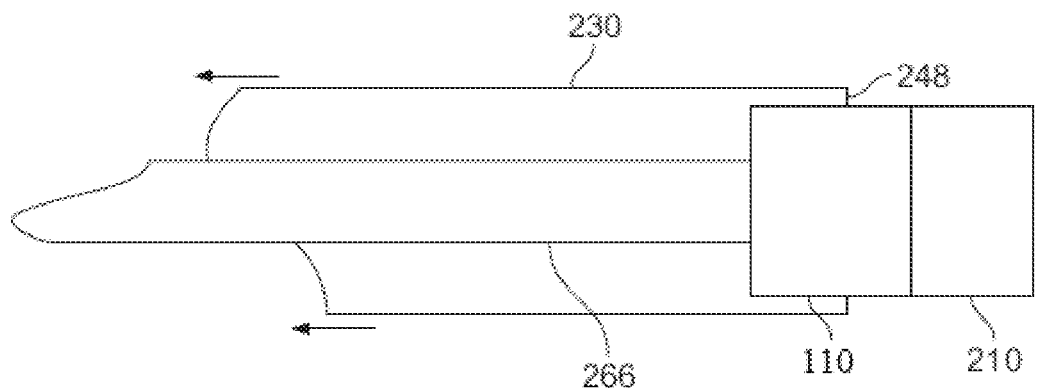

FIGS. 16-20 illustrate anchor 210 in progressive stages of deployment from the open end 248 of tube 230. Tube 230 is shown in a distalmost position in FIG. 16, with open end 248 positioned outside of heart 234. Tube 230 may be retracted while anchor 210 is forced to remain in place, such as by a reversal of a typical Bowden cable arrangement. For example, a semi-rigid cable or wire 266 may be inserted through tube 230 to contact the proximal end of anchor 210, as shown in FIG. 21A. Pulling tube 230 proximally relative to wire 266 causes anchor 210 to deploy out from the open end 248 of tube 230, as shown in 21B. As shown in FIG. 17, retracting tube 230 while preventing anchor 210 from retreating with the tube into heart 234 causes first disc 214 of anchor 210 to deploy out from the open end 248 of tube 230 and expand radially relative to axis X. Upon further retraction of tube 230, the bias of first disc 214 causes it to curve back onto the outer apex 246 of heart 234, as shown in FIG. 18. Further retraction of tube 230 in FIG. 19 allows second disc 218 to deploy and expand radially relative to axis X within left ventricle 242 until second disc 218 opens to press against an inner side of wall 238, as shown in FIG. 20. Pressure against wall 238 results from the elastic bias of first disc 214 and second disc 218 toward certain resting positions as described above with regard to FIGS. 11A, 11B, and 12. First disc 214 and second disc 218 pressing on opposite sides of wall 238 causes anchor 210 to grip wall 238. Such progressive expansion from within a narrow tube results in anchor 210 adequately securing valve 110 to ventricular wall 238 without requiring an intercostal puncture through the patient's chest.

In the trans-jugular and trans-femoral delivery routes described above, one end of the tether 226 is preferably fixed to the anchor 210 before deployment of the anchor 210, including prior to loading the valve 110 into tube 230. Tether 226 and anchor 210 remain attached while anchor 210 is delivered to the exterior of ventricular wall 238 from within tube 230, and tether 226 is uncovered by the retraction of tube 230. In alternate embodiments, the anchor 210 and tether 226 may be fixed to one another during or immediately after deployment of the anchor 210. The tether 226 may extend proximally to a second free end, and the prosthetic valve 110 is preferably delivered over the tether 226, using the tether 226 as a rail and/or guide, with the tether 226 extending through a center portion of prosthetic valve 110 while the valve 110 is being delivered to the native valve annulus. Once the prosthetic valve 110 is at or adjacent the final position within the native valve annulus, the prosthetic valve 110 is preferably fixed to the tether 226 by engagement or activation of the tether connecting portion 144 with the tether 226. This engagement may be accomplished via one or more mechanisms, including those described below, and the engagement may occur just before, during, or just after deployment of the prosthetic valve 110. Much of the below disclosure relates to a further embodiment of tether connecting portion 144 to facilitate such a connection between the prosthetic valve 110 and the second end of the tether 226. Placement of valve 110 into native mitral valve 260 may involve affixing tether 226 to anchor 210 at one end of tether 226, as noted above. It may also involve affixing tether 226 to a tensioning mechanism (not shown) at the other end of tether 226. The tensioning mechanism may include a load sensor for measuring tension and will remain outside the body of the patient while anchor 210 is inserted through one of the above-mentioned methods. Although it should be understood that the tensioning mechanism may be affixed to the tether after the anchor 210 is deployed. Thus, after anchor 210 is secured against outer apex 246 of heart 234, tether 226 may extend from anchor 210 to the tensioning mechanism, e.g., the entire length of the path used to insert anchor 210 against outer apex 246. One example using an above-mentioned method may embody tether 226 extending from anchor 210 through ventricular wall 238, left ventricle 242, native mitral valve 260, left atrium 256, atrial septum 254, right atrium 252, superior vena cava 236, exiting the patient through a jugular vein (not shown) and attaching to the tensioning mechanism outside the patient. Maintenance of tether 226 in this position may permit valve 110 to attach to tether 226 outside the patient's body, using tether 226 as a guide to follow the path of tether 226 to place valve 110 within native mitral valve 260. Several embodiments of how valve 110 may be secured into place in native mitral valve 260 will be explained below in further detail. It should be understood that, if the prosthetic valve 110 is fixed to the tether 226 after the anchor 210 is deployed and the prosthetic valve 110 is at or near its final desired position, it may be preferable to fix the prosthetic valve 110 to the tether 226 by activating or engaging the tether connecting portion 144 to the tether 226 after the tether 226 has been tensioned a desired amount, at which point the coupling of the tether connecting portion 144 of the prosthetic valve 110 to the tether 226 will maintain the desired tension in the tether 226. Such tension may provide certain benefits, for example helping to prevent the prosthetic valve 110 from migrating into the atrium. The force on the ventricle from the tension of the tether 226 may also facilitate more efficient functioning of the ventricle. Various mechanisms for fixing the prosthetic valve 110 to the tether 226 after the tether 226 has been tensioned are described in greater detail below.

Figure 22:
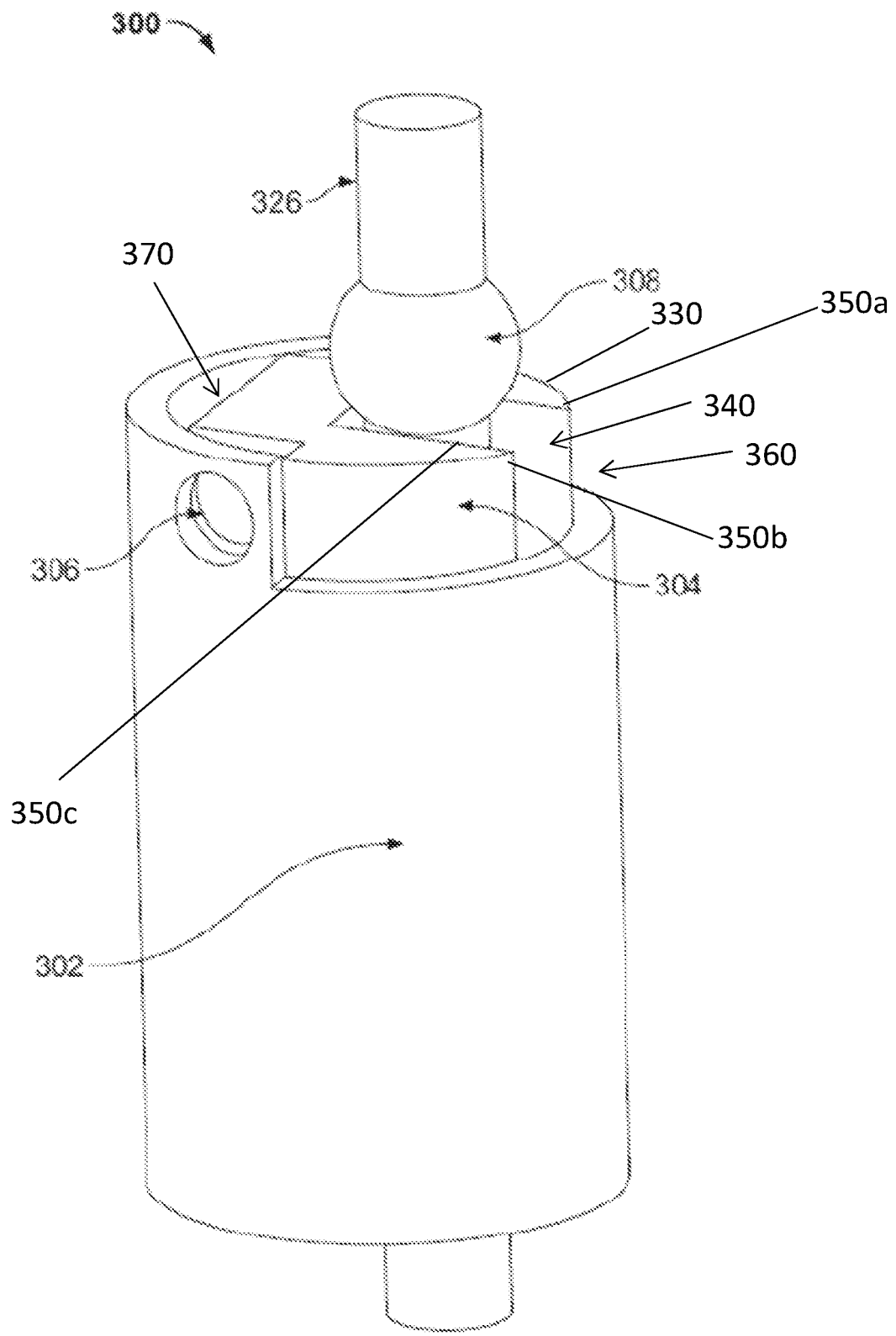
FIGS. 22-23 are perspective views of a ball and flap mechanism on a tether connecting portion of the valve interacting with a tether in a closed and opened state, respectively.
Figure 23:
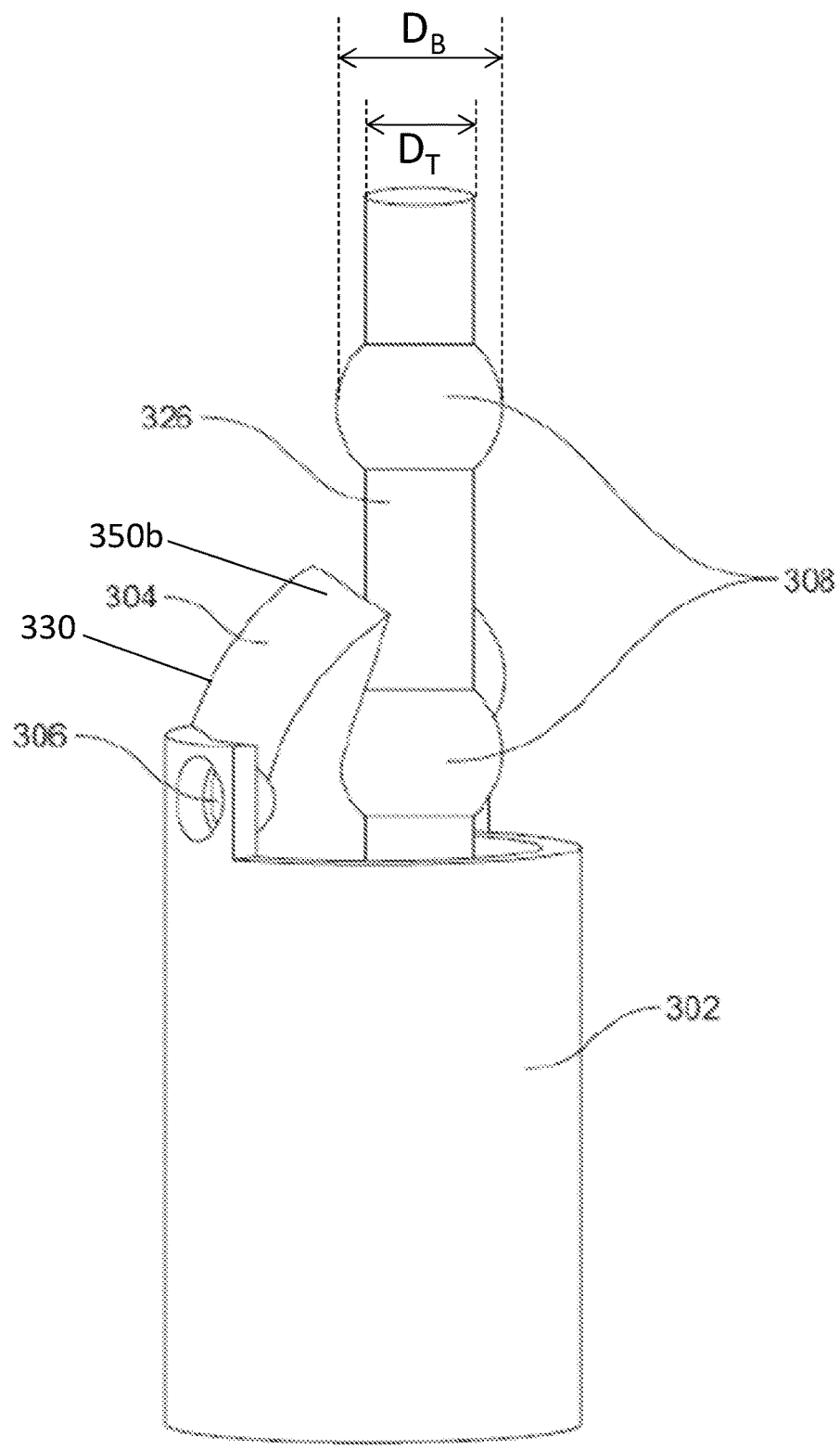
Figure 24:
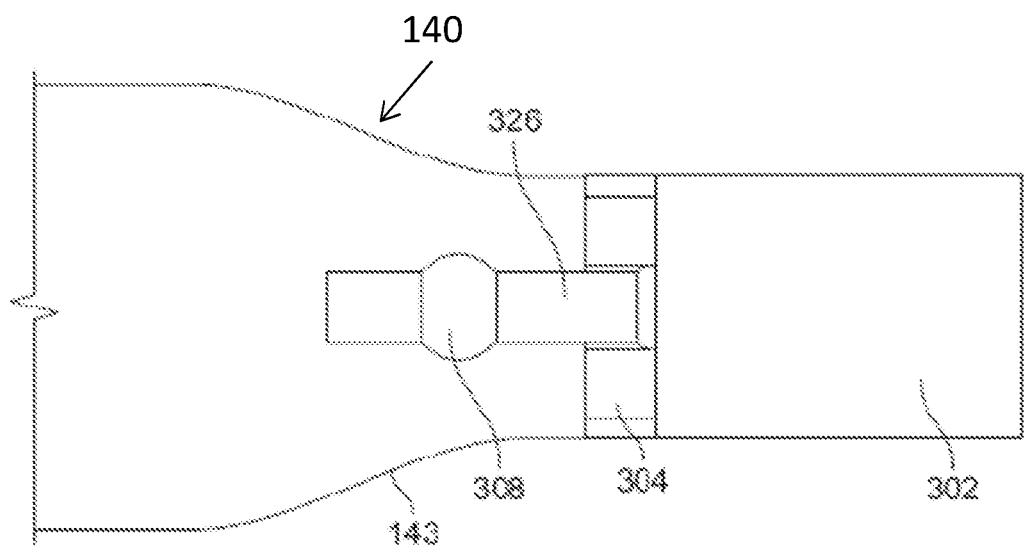
FIG. 24 is a side view of the ball and flap mechanism on the tether connecting portion while attached to the prosthetic valve.

FIGS. 22-24 show an embodiment of a tether connecting mechanism 300 for coupling a prosthetic heart valve similar to valve 110 to a tether 326 similar to tether 226. In the illustrated embodiment, tether connecting mechanism 300 takes the form of a ball and flap mechanism 300. The ball and flap mechanism 300 may function to secure valve 110 in native mitral valve 260 with desired tension on tether 326. Ball and flap mechanism 300 may be attached to strut portion 143 of valve 110 on the end of valve 110 nearest anchor 210, i.e. the outflow end, as shown in FIG. 24. In other words, the ball and flap mechanism 300 may either replace the tether connecting portion 144 of inner frame 140, or may be positioned within the tether connecting portion 144 of inner frame 140. Tether 326 may be substantially similar or identical to tether 226, with at least one exception. For example, at least a portion of tether 326 may include balls 308, or other protrusions or enlarged-width structures, spaced from one another along the length of tether 326. In one embodiment, the balls 308 are only positioned along the portion of tether 326 that is expected to engage the ball and flap mechanism 300. As is described in greater detail below, the balls 308 facilitate connection between the tether 326 and the prosthetic valve 110, as well as facilitating the maintenance of a desired tension on the tether 326. Tether 326 is not limited to the use of balls 308; other examples may include knots, beads, other clamp-on pieces, etc. Ball and flap mechanism 300 may include a flap 304 hingedly coupled to valve stem body 302, for example by hinge 306. Flap 304 may be in a closed position when flap 304 sits generally perpendicular to a central longitudinal axis of valve stem body 302, as shown in FIG. 22. Flap 304 may be in an open position when flap 304 sits generally parallel to the longitudinal axis of valve stem body 302 as shown in FIG. 23. In some embodiments, flap 304 may be biased into a closed position by a biasing member, for example a torsion spring (not shown). In the illustrated embodiment, flap 304 has a free end 360 generally opposite the end 370 where hinge 306 couples the flap 304 to the valve stem body 302. The free end of the flap 304 may have a generally circular circumference 330 that is interrupted by a substantially "U"-shaped recessed portion 340, with two free arms 350a, 350b of the flap defining portions of the "U"-shaped recess. The recessed portion may be adapted to receive a portion of tether 326 therethrough, as shown in FIG. 22. The "U"-shaped recessed portion may have a width defined between inner edges 350c of the two free arms, the width of the recessed portion being greater than a diameter $D_T$ of the tether 326, but smaller than a diameter $D_B$ of the balls 308.

As noted above, after the anchor 210 has been deployed, the prosthetic valve 110 may be guided over the tether 326 toward the mitral valve 260, for example, while collapsed in a sheath of a delivery device, with the delivery device sheath and the prosthetic valve 110 being fed over the tether 326. During this delivery, the tether 326 may be held taut, for example manually or via a tensioning mechanism coupled to the tether 326. During delivery, the valve stem body 302 may be the leading end of the prosthetic valve 110. As the valve stem body 302 approaches and slides over the balls 308 of the tether 326, the first encountered ball 308 may cause the flap 304 to open. If the flap 304 is biased toward the closed condition, it will begin to close as soon as the recessed portion of the flap 304 clears the ball 308. The flap 304 may be biased toward the closed condition by a torsion spring. Alternatively, the flap 304 may be coupled to the tether 326 such that the tension in the tether 326 may bias the flap 304 toward the closed condition. As the prosthetic valve 110 continues to approach the native mitral valve 260, the flap 304 may continue opening and closing as it passes successive balls 308 on the tether 326. The prosthetic valve 110 is advanced until it reaches the desired position within the native mitral valve 260. It should be understood that, depending on the position of the balls 308 on tether 326, the prosthetic valve 110 may reach the desired position in the native mitral valve 260 without encountering any of the balls 308. Maintaining a level of tension on the tether 326 while the prosthetic valve 110 is being advanced distally over the tether 326 may help ensure that the flap 304 does not cause the tether 326 to be pushed distally, but rather the balls 308 of the tether 326 cause the flap to open upon contact between the flap 304 and ball 308.

After prosthetic valve 110 has reached the desired position in native mitral valve 260, the prosthetic valve may be ejected from the delivery device and expand (for example via self-expansion or balloon expansion) into the annulus of the native mitral valve 260. Once the position and/or orientation of the prosthetic valve 110 is confirmed as desired, the tether 326 may be tensioned. Tensioning the tether 326 may include pulling the tether 326 proximally, for example manually or via a tensioning tool coupled to the free end of the tether 326. In some embodiments, the tensioning tool may grip a portion of the tether 326, with a portion of the tensioning tool being rotated or otherwise activated to pull the tether 326, preferably with a measurement of the tension being measured during the process, for example via a load cell. As the tether 326 is tensioned, the pulling/tensioning force causes tether 326 and associated balls 308 to translate proximally relative to the valve stem body 302 of prosthetic valve 110 while the prosthetic valve 110 is held in place in native mitral valve 260. As each ball 308 passes proximally through valve stem body 302, and the relatively large diameter of the ball 308 is unable to pass through the recessed portion of flap 304, resulting in the flap 304 moving into the open position, with hinge 306 facilitating flap 304 moving into the open position. While the flap 304 is in the open position, the ball 308 is permitted to pass proximally through ball and flap mechanism 300 as demonstrated in FIG. 23. After a ball 308 clears flap 304, flap 304 may return to a closed position, for example via the biasing force of the hinge 306. While flap 304 sits in the closed position, flap 304 does not permit ball 308 to pass distally through the recessed portion of flap 304 or valve stem body 302. This may be accomplished, for example, via a rim, shoulder or ledge in the proximal end of valve stem body 302 defined by a valve stem body 302 opening that is smaller than the outer circumferences of the flap 304, so that an outer edge portion of flap 304 abuts the rim of the proximal end of the valve stem body 302 in the closed condition. The tether 326 may be continued to be pulled proximally to further tension the tether 326 until a desired tension on tether 326 is achieved between anchor 210 and valve 110. The level of desired tension may be determined via any suitable method, including for example a display on the tensioning mechanism that outputs a tension force as the tether 326 is tensioned.

While the tether 326 is being tensioned, the contact between the balls 308 and the flap 304 may tend to pull the valve stem body 302, and the connected prosthetic valve 110, proximally in the direction that the tether 326 is being pulled. In some embodiments, the flap 304 may move freely enough that pulling the tether 326 does not tend to move the prosthetic valve 110. For example, the frictional force between the expansion of the prosthetic valve 110 and the annulus of the native mitral valve 260 may be large enough to ensure that the force of the balls 308 pulling against flap 304 does not tend to move the prosthetic valve 110 in the direction that the tether 326 is being pulled. In other embodiments, a separate tool may be provided, for example as part of the delivery system, to contact the prosthetic valve 110 to provide a counteracting force to maintain the prosthetic valve 110 in the desired position as the tether 326 is pulled proximally. Once the tether 326 reaches the desired tension, tension on the tether 326 may be released, causing the tether 326 to tend to move distally through the valve stem body 302. However, as noted above, the balls 308 of the tether 326 are unable to pass through the flap 304 in the distal direction since the flap 304 is in abutment with the proximal end of the valve stem body 302. Thus, the contact between one of the balls 308 and the proximal face of flap 304 may result in tension being maintained and the flap 304 being maintained in the closed condition, particularly if the flap 304 is not actively biased toward the closed condition.

If it is determined that the tension on the tether 326 is too large, the tension may be relieved by any suitable mechanism. For example, a tool may be introduced via the delivery device (or a separate delivery device) to a position adjacent the valve stem body 302, and the tool may be used to pull or otherwise hold flap 304 in the open position to allow balls 308 and tether 326 to pass distally through ball and flap mechanism 300 in order to reintroduce slack (or otherwise reduce tension) in tether 326 between valve 110 and anchor 210. Whether or not the tension is readjusted in this manner, once the tension is at the final desired level and the tether 326 does not need to be further adjusted with respect to the ball and flap mechanism 300, excess length of the tether proximal to the flap 304 may be removed by any suitable mechanism. For example, a tool may be utilized to cut the excess length of tether 326 extending proximally from valve 110 via cautery or mechanical cutting, with the entire length of the tether 326 proximal to the position of the cut to be removed from the patient.

Figure 25:
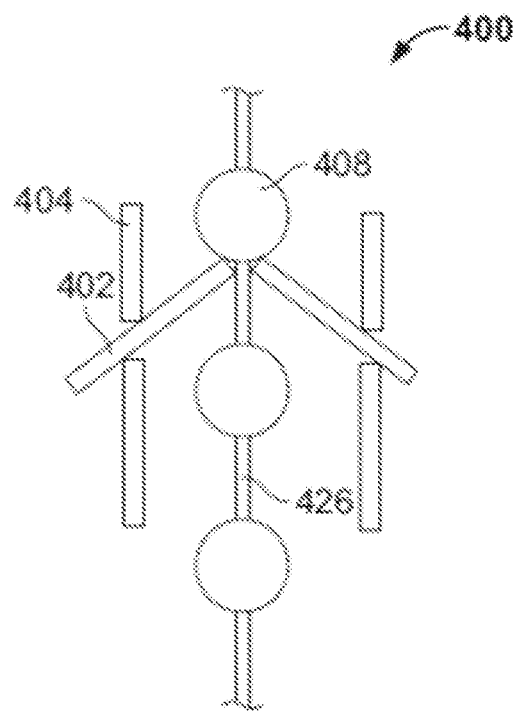
FIG. 25 is a cross-section of a tabbed valve stem on the tether connecting portion of the prosthetic valve interacting with the tether.

FIG. 25 shows a tabbed valve stem 400, which may provide similar functionality as the ball and flap mechanism 300 described above. In the illustrated embodiment, tabbed valve stem 400 may be substantially similar to connecting portion 144 described above, with certain exceptions. For example, tabbed valve stem 400 can be formed from a milled or laser-cut tube of a shape-memory material such as, for example, nitinol, similar or identical to that described above in connection with connecting portion 144. Tabbed valve stem 400 may form a substantially cylindrical structure, and may include the micro-V's described above in connection with connecting portion 144, or similar structures. However, while connecting portion 144 may form an entirely cylindrical passageway therethrough, tabbed valve stem 400 may include structures extending into the interior passage of the tabbed valve stem 400. In the view of FIG. 25, a cross-section of the tabbed valve stem 400 is illustrated with tether 426 passing therethrough. In the orientation of FIG. 25, the bottom of the tabbed valve stem 400 represents the outflow end of the prosthetic valve, while the remainder of the inner frame 140, which would extend from the top of the tabbed valve stem 400, is omitted from the drawing. The other components of the prosthetic valve, such as the outer frame 170, are also omitted from the figure for purposes of clarity. Tabs 402 may be laser cut into the nitinol tube portion 404 of tabbed valve stem 400. For example, tabs 402 may be substantially "V"-shaped similar to the micro-V's described above. In the illustrated embodiment, tabs 402 are shaped so that the apex of the "V"-shape is pointed substantially in the proximal direction (toward the top of the page in the view of FIG. 25) while the opposite end of the "V"-shape is pointed substantially in the distal direction (toward the bottom of the page in the view of FIG. 25). In other words, the tabs 402 may be formed integrally with tubing 404, although in other embodiments, the tabs 402 may be formed separately and attached to tubing 404. Although a substantial "V"-shape is described, other shapes may be suitable, including linear bar shapes, or any other suitable shape. The tabs 402 may each be shape set such that, in the absence of applied forces, tabs 402 form an angle transverse to tubing 404. While in this shape set condition, the ends of tabs 402 facing radially inward may point in a generally proximal direction, while the ends of tabs 402 facing radially outward may point in a generally distal direction. Tabbed valve system 400 may function in a similar fashion to ball and flap mechanism 300 described above. For example, tether 426 may be similar or identical to tether 326 and may similarly include balls 408 spaced along tether 426. The delivery of the prosthetic valve 110 may be substantially identical as described above in connection with ball and flap mechanism 300. For example, when tension is applied to the tether 426 by pulling the tether 426 proximally, tabs 402 may pivot about their connection to tubing 404 to separate, permitting balls 408 to pass beyond the tabs 402. In one example, the tabs 402 may be pivotably connected to tubing 404 at a point nearer the distal end of the tabs 402 than the proximal end of the tabs 402. When in the set shape, in the absence of applied forces, the distance between the proximal ends of the tabs 402 may be smaller than the diameter of the balls 408, but larger than the diameter of the portions of tether 426 between adjacent balls 408. Thus, as the tether 426 moves proximally relative to the tabs 402, the balls 408 will cause the tabs 408 to separate. After ball 408 has completely cleared or passed tabs 402, tabs 402 may return to a resting position, for example against tether 426. When the pulling force on tether 426 is released, and the tether 426 is tensioned, the tether 426 will tend to try to move distally with respect to tabs 402 to release the tension. However, due to their set shape, the tabs 402 will not permit balls 408 to move distally past tabs 402. Proximal pulling of the tether 426 may continue until a desired tension on tether 426 is reached between anchor 210 and valve 110. Then, upon releasing the tether 426, the tabs 402 will maintain the tether 426 in or near the desired tension by preventing distal movement of the tether 426 relative to the tabs 402. The ends of tabs 402 facing radially outward (or generally distally) may extend radially beyond the outer perimeter of the tubing 404, such that the outward ends of tabs 402 may be compressed to force tabs 402 to pivot into the substantially open position in order to allow balls 408 to translate distally through tubing 400 to reintroduce slack in tether 426 between valve 110 and anchor 210. A tool may be utilized to cut excess tether 426 extending proximally from valve 110 via cautery or mechanical cutting, with the entire length of the tether 426 proximal to the position of the cut to be removed from the patient.

Figure 26:
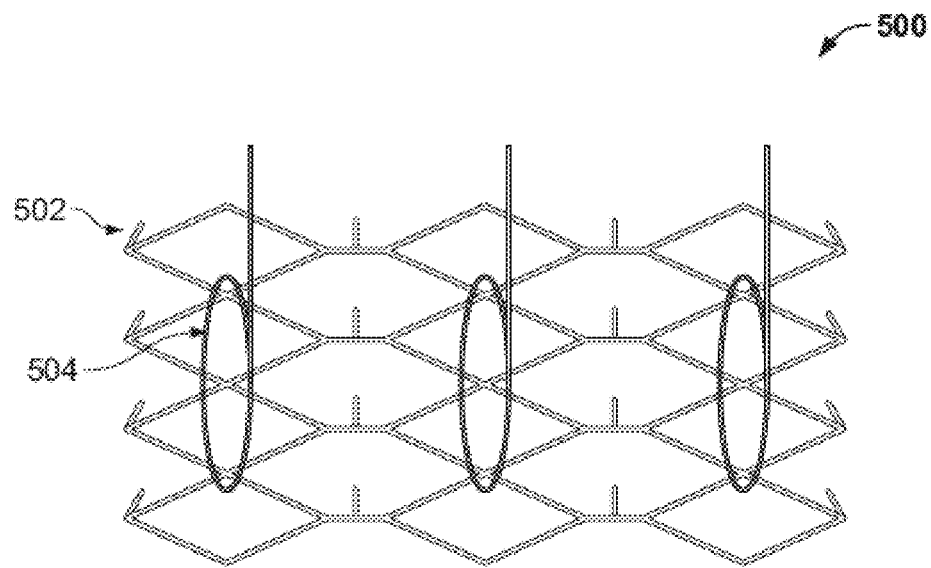
FIGS. 26-27 are opened and flattened views of a barbed valve stem on the tether connecting portion while the prosthetic valve is in a compressed delivery state and an expanded deployed state, respectively.
Figure 27:
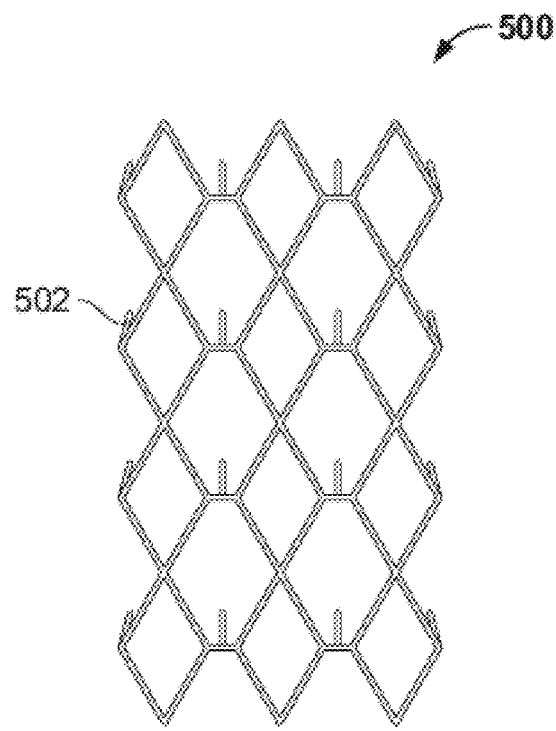

FIGS. 26-27 show a barbed valve stem 500, which may be provided on prosthetic valve 110 as an alternate embodiment of tether connecting portion 144. Although the remainder of prosthetic heart valve 110 is omitted from FIGS. 26-27, it should be understood that barbed valve stem 500 is positioned at or near the outflow end of the prosthetic valve 110 (toward the bottom in the view of FIGS. 26-27), while the remainder of the valve would be positioned above the barbed valve stem 500 in the view of FIGS. 26-27. Barbed valve stem 500 can be formed from a milled or laser-cut tube of a shape-memory material such as, for example, nitinol. Preferably, barbed valve stem 500 is formed integrally with the inner frame 140, although in some embodiments, the barbed valve stem 500 may be formed separately and attached to inner frame 140. Barbed valve stem 500 may be cut into diamond cells that allow it to compress and expand, for example via self-expansion via shape-memory material properties or via mechanical compression or expansion via a suitable mechanical device.

Barbed valve stem is shown in FIGS. 26-27 as if unrolled into a flat sheet for ease of illustration, although it should be understood that, in practice, the barbed valve stem 500 is generally tubular. In FIG. 26, barbed valve stem 500 is illustrated in an axially collapsed, radially expanded condition. This condition may also correspond to the delivery condition of the prosthetic valve 110. It should be noted that, although the barbed valve stem 500 is in an axially collapsed, radially expanded condition during delivery, the remainder of the prosthetic valve 110 is in an axially expanded, radially collapsed condition during delivery. Even when the barbed valve stem 500 is in a radially expanded condition, the diameter or profile of the barbed valve stem 500 is smaller than the diameter of the remainder of the prosthetic valve 110 while the remainder of the prosthetic valve 110 is in the radially collapsed condition. As a result, maintaining the barbed valve stem 500 in a radially expanded condition during delivery does not negatively affect the overall delivery profile of the prosthetic valve 110. Barbed valve stem 500 may be shape set as to tend to transition to the radially collapsed condition shown in FIG. 27. Thus, the barbed valve stem 500 may need to be maintained or held in the radially expanded condition during delivery of the prosthetic valve 110. One mechanism by which the barbed valve stem 500 may be maintained in the radially expanded condition (or the axially collapsed condition) is at least one suture loop 504 which may loop around points of barbed valve stem 500 and extend proximally to be accessible to a surgeon. In the illustrated example, barbed valve stem 500 is maintained in the radially expanded condition by three suture loops 504, with each suture loop having two free ends that extend through the delivery system. For example, each suture loop 504 may have a middle portion that loops one or more times around apices of diamond-shaped cells to axially compress those cells. In one example, each suture loop may loop through a distalmost and proximal-most cell in the barbed valve stem 500. The suture loops 504 may be forced into a relatively small loop circumference in order to draw the cells closer together, and thus maintain the barbed valve stem 500 in the axially compressed (and radially expanded) condition. The barbed valve stem 500 may include a plurality of barbs 502 that have a first end connected to the barbed valve stem 500 and a second free end opposite the first end. The second free end of the barbs 502 may be sharp or pointed in order to allow the barbs 502 to pierce the tether. In the illustrated embodiment, each barb 502 is connected to the barbed valve stem 500 at intersections of adjacent cells. The barbs 502 are preferably integral with the barbed valve stem 500, for example via laser cutting the entire barbed valve stem 500, including barbs 502, from a tube of nitinol or other suitable metal. The barbs 502 are also preferably shape set so that, in the absence of applied forces, they tend to point radially inwardly and proximally. With this configuration, a tether may be able to slide proximally relative to the barbed valve stem 500, even when the barbs 502 are in contact with the tether. However, the barbs 502 may engage and/or pierce the tether when the tether tries to slide distally relative to the barbed valve stem 500 when the barbs 502 are in contact with the tether. Alternatively, barbed valve stem 500 may fixedly attach to the tether when the barbed valve stem 500 is radially compressed and the barbs 502 engage or pierce the tether, such contact between the barbs 502 and the tether prohibiting the prosthetic valve 110 from translating in either direction relative to the tether. When forced into the axially compressed state, the diameter of barbed valve stem 500 may increase, resulting in the sharp free ends of the barbs 502 being spaced apart from the tether. Thus, in this axially compressed condition, a tether passing through the barbed valve stem 500 will not contact (or will not significantly contact) the barbs 502 enough to cause the barbs 502 to engage or pierce the tether. This allows the tether to translate proximally or distally relative to the barbed valve stem 500 when the barbed valve stem 500 is in the radially expanded condition without the barbs 502 significantly hindering such movement.

Barbed valve stem 500 is shown in an axially expanded, radially collapsed, deployed condition in the flattened view of FIG. 27. As noted above, barbed valve stem 500 may be at rest (or have its set shape) when in the radially collapsed state, and may have an inner diameter smaller than (or about equal to) that of the outer diameter of tether to bring the second free ends of the barbs 502 into contact with the tether. During delivery, the suture loops 504 may remain in place (and maintain the barbed valve stem 500 in the radially expanded condition) until prosthetic valve 110 has been positioned at the desired location within the native mitral valve annulus and the desired tension of the tether between anchor 210 and prosthetic valve 110 has been achieved. With the prosthetic valve 110 otherwise in its final desired condition, the suture loop(s) 504 may be released, allowing the barbed valve stem 500 to axially expand and radially collapse, bringing the sharp ends of the barbs 502 into contact with the tether. The suture loops 504 may be released by releasing the grip on one of the free ends of the suture loops 504, and pulling the other free end of the suture loop 504 proximally. As the one free end of the suture loop 504 is pulled, the other free end of the suture loop 504 travels toward the barbed valve stem 500, causing the loops or turns around the cells of the barbed valve stem 500 to unravel or uncoil, and eventually the released free end of the suture loop 504 will pull back through the delivery device and outside of the patient. After the suture loops 504 are released and the barbed valve stem 500 radially collapses, the pulling force on the tether that maintains the tether in the tensioned condition may be released. Upon release of that pulling force, the tether will tend to try to translate distally with respect to the barbed valve stem 500 to release the tension. However, because the sharp ends of the barbs 502 are in contact with the tether, the barbs will engage or pierce the tether (which may be formed of a relatively soft fabric and/or polymer) preventing the tether from translating any significant distance in the distal direction. While the barbs 502 engage the tether, the tension on the tether is maintained at or near the desired level, and the tether is prevented from translating distally relative to the prosthetic valve 110. If it becomes necessary to release the barbs 502 from the tether, for example to re-position or remove the prosthetic valve 110, a tool may be introduced to axially compress barbed valve stem 500 to force the barbed valve stem 500 to radially expand, moving the barbs 502 out of engagement with the tether.

Figure 28:
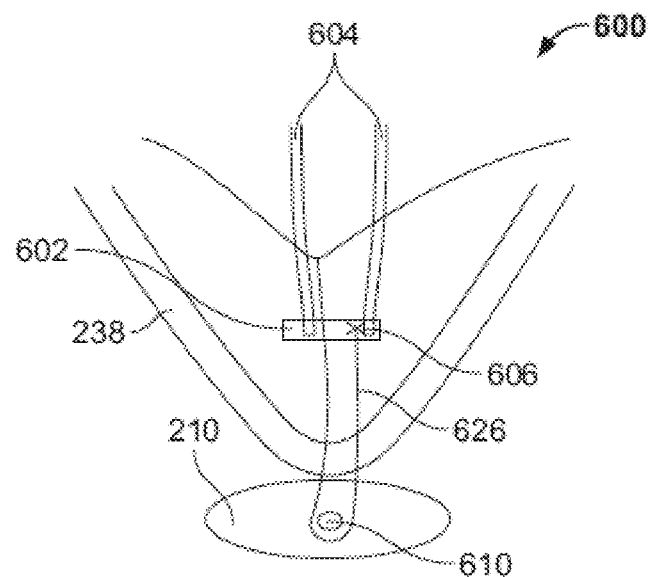
FIGS. 28-29 are side views of a guy-line tensioner interacting with the tether in an open and closed state, respectively.
Figure 29:
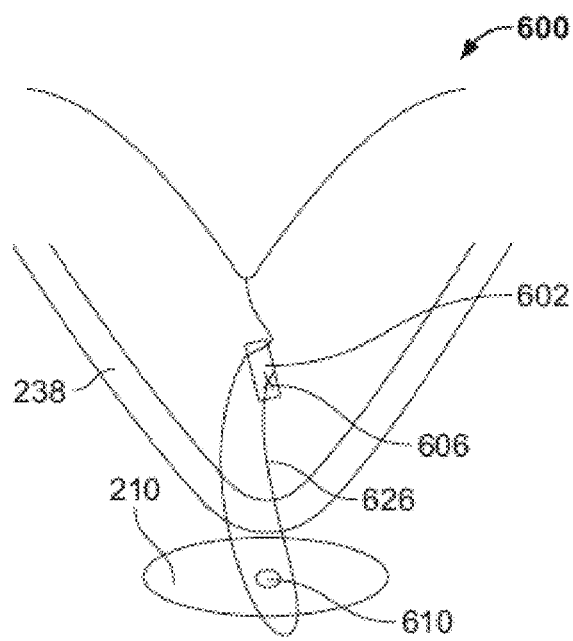
Figure 30:
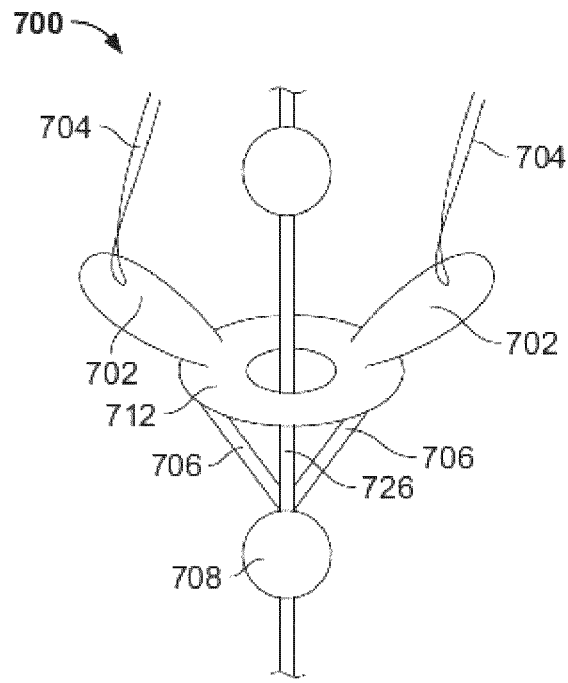
FIGS. 30-31 are side views of a clutch mechanism interacting with a knotted tether in a closed and open state, respectively.

FIGS. 28-29 show guy-line tensioner 600, which may be used with prosthetic valve 110, either in addition to tether connecting portion 144, or an alternate embodiment of tether connecting portion 144. Guy-line tensioner 600 may include a tether 626 that is fixed to prosthetic valve 110 at or near the outflow end of the prosthetic valve 110. For example, a first end of the tether 626 may be fixed to tether connecting portion 144 or to a similar structure. The tether 626 may be threaded through a tension clip 602, for example through a first hole or aperture in the tension clip 602. In one embodiment, the tension clip 602 has a substantially rectangular or oval shape, although other shapes may be suitable. The tension clip 602 may include relatively large front and back faces, with a first aperture extending through the tension clip 602 from the front face to the back face near a first end of the tension clip 602. The tension clip 602 may include a second aperture extending through the tension clip 602 from the front face to the back face near a second end of the tension clip 602 opposite the first end. After the tether 626 passes through the first aperture, it may then loop around pad pulley 610, with the second end 606 of the tether 626 fixed to tension clip 602. Tension clip 602 may be configured such that when tension clip 602 is substantially parallel to a longitudinal axis of the prosthetic valve 110, a relatively large amount of friction exists between tether 626 and tension clip 602, the friction being large enough to prevent translation of tether 626 through tension clip 602. This is the condition illustrated in FIG. 29.

As shown in FIG. 28, tension clip 602 may also be configured to be lifted and/or adjusted by one or more suture loops 604 such that tension clip 602 is no longer substantially parallel to the longitudinal axis of the prosthetic valve 110. Each suture loop 604 may have two free ends and a middle portion therebetween, with the middle portion wrapping or looping around a corresponding aperture or other loop-receiving structure in tension clip 602. As is described in greater detail below, as the tension clip 602 is adjusted from the position shown in FIG. 29 toward the position shown in FIG. 28, friction between the tether 626 and the tension clip 602 reduces, allowing for the tension clip 602 to translate toward the prosthetic valve 110, or alternatively allowing the prosthetic valve 110 to translate toward the tension clip 602. Thus, with tension clip 602 in an adjusted position, friction may decrease between tether 626 and tension clip 602, allowing tether 626 to translate through tension clip 602 to modify tension on tether 626. In the illustrated embodiment, guy-line tensioner 600 includes a first suture loop 604 for adjusting the orientation of tension clip 602 to modify the friction between the tension clip 602 and the tether 626, and a second suture loop 604 for translating the tension clip 602 along tether 626 for increasing or decreasing tension in the tether. Tension in the tether 626 may be sufficient to translate the tension clip 602 without any manipulation of the second suture loop 604 when the tension clip 602 is in an adjusted position. For example, modifying the tension clip 602 from its resting position to an adjusted position may release tension in the tether 626, and tension on the second suture loop 604 may be exerted to preserve a desired level of tension on the tether 626. In order to assist in changing the orientation of the tension clip 602, the suture loop 604 for adjusting orientation is preferably connected to the tension clip 602 near where the second end 606 of the tether 626 couples to the tension clip 602. In order to assist in translating the tension clip 602 to modify the tension of the tether 626, the suture loop 604 for modifying tension is preferably connected to the tension clip 602 close to where the tether 626 passes through the tension clip 602.

Anchor 210 may be deployed around the exterior surface of ventricular wall 238, in a fashion similar or identical to the a method described above, with the tether 626 already passing through the tension clip 602, wrapping around the pad pulley 610, and the second end 606 of the tether 626 already affixed to the tension clip 602. The pad pulley 610 may take the form of a rotatable pulley structure, or a static low friction surface around which the tether 626 wraps or loops. The pad pulley 610 functions to serve as an anchor point for the tether 626 while allowing (or at least not inhibiting) movement of the tether 626 during tension modification. The suture loops 604 may also be attached to the tension clip 602 prior to delivery and remain in place until the anchor 210 and the prosthetic valve 110 have both been deployed. Upon initial deployment of the prosthetic valve 110, the tension clip 602 may be positioned with respect to tether 626 so that the tether 626 has enough slack to ensure that the prosthetic valve 110 is able to be positioned within the native valve annulus while the anchor 210 is deployed. After the initial deployment of the prosthetic valve 110 and the confirmation of the desired positioning, the tether 626 may be tensioned to the desired amount. In order to tension the tether 626, the suture loop 604 for adjusting the orientation of the tension clip 602 may be pulled proximally, transitioning the tension clip 602 from the orientation shown in FIG. 29 to the orientation shown in FIG. 28. As noted above, when tension clip 602 is angled at or near orthogonal to the longitudinal axis of the prosthetic valve 110 (as shown in FIG. 28), friction between the tether 626 and the tension clip 602 where the tether 626 passes through the tension clip 602 is reduced compared to when the tension clip 602 is substantially parallel to the longitudinal axis of the prosthetic valve 110. While the orientation of the tension clip 602 is maintained in the orientation shown in FIG. 28, the other suture loop 604, which is connected to the tension clip 602 near where the tether 626 passes through the tension clip 602, may be pulled proximally. Proximal pulling of this suture loop 604 will tend to draw the tension clip 602 toward the prosthetic valve 110. Since both ends of the tether 626 are fixed, as the tension clip 602 translates toward the prosthetic valve 110, tension on the tether 626 increases. Once the desired tension of tether 626 between anchor 210 and valve 110 has been achieved, the suture loops 604 connected to tension clip 602 near the second end 606 of the tether 626 may be released, allowing the tension clip to again change orientation, from the orientation shown in FIG. 28 to the orientation shown in FIG. 29. In the orientation of FIG. 29, the friction between tether 626 and tension clip 602 increases, such that the force due to friction is larger than the force due to tension, resulting in the tension clip 602 maintaining its position so that the tether 626 remains at the desired tension. Then, the other suture loop 604 may also be released, for example by pulling one end of suture loop 604 proximally until it vacates the patient's body. After both suture loops 604 are released and withdrawn from the patient's body, as shown in FIG. 29, tension clip 602 is in a resting position where tension clip 602 is substantially parallel to the longitudinal axis of prosthetic valve 110, preventing tether 626 from translating through tension clip 602 while maintaining a consistent distance with desired tension in tether 626 between valve 110 and anchor 210.

Figure 31:
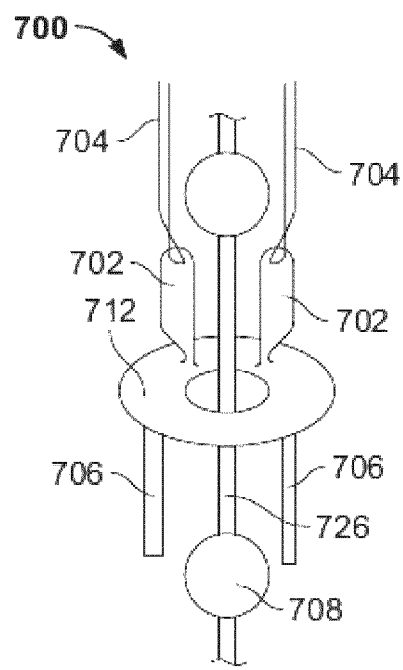
Figure 32:
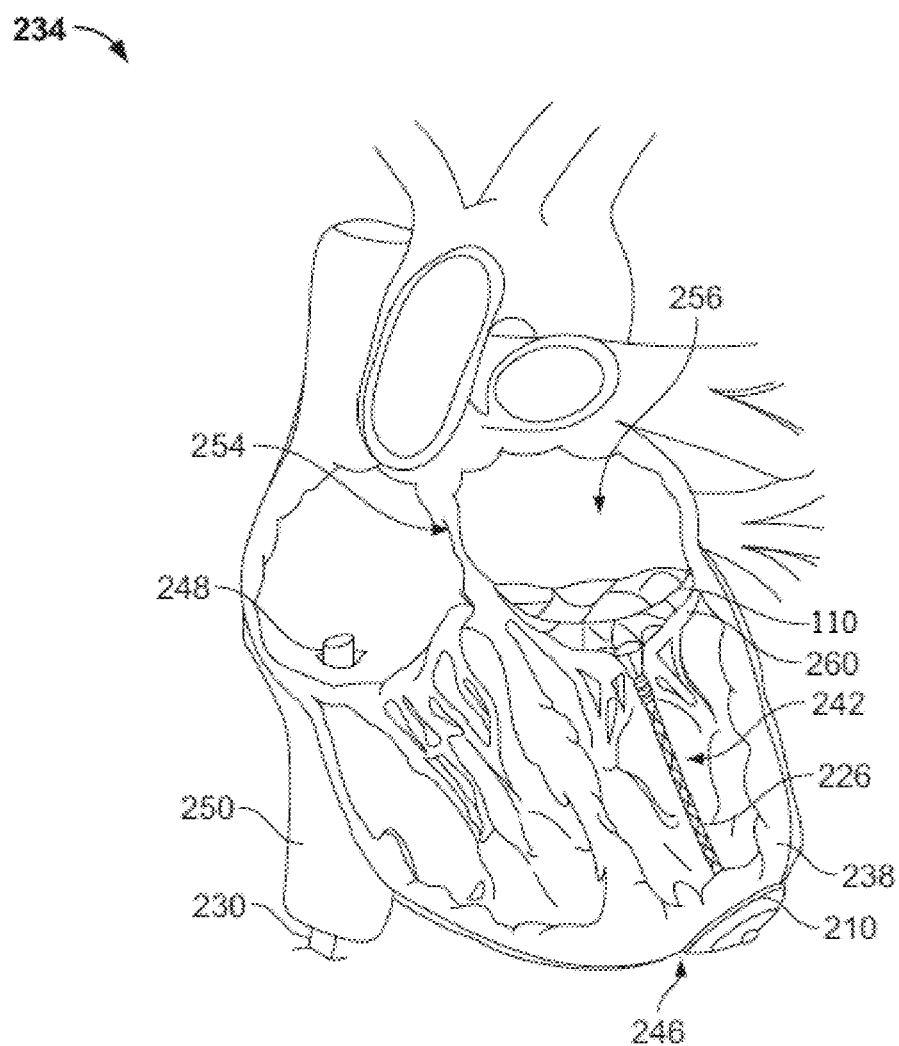
FIG. 32 illustrates the valve of FIG. 1 implanted in a heart.

FIGS. 31-32 show a clutch mechanism 700, an alternative mechanism for securing a tether at a desired tension. The clutch mechanism 700 could be provided within (or adjacent to) tether connecting portion 144 of inner frame 140, or as an alternative to tether connecting portion 144. Clutch mechanism 700 may be substantially similar in function to butterfly clutch pin backs. Clutch mechanism 700 may include a substantially flat, annular base 712 that defines an opening through which tether 726 is configured to pass. When the tether 726 passes through the annular base 712 of the clutch mechanism 700, the base 712 circumscribes tether 726. The clutch mechanism 700 may include plates 706 extending in the outflow direction from the annular base 712 of clutch mechanism 700. When there is no force applied to the plates 706, the plates 706 may have free ends that point radially inwardly toward tether 726. Each respective plate 706 may be operably coupled, for example via a hinge, to a corresponding wing 702. Each wing 702 may extend in the inflow direction from the annular base 712 of clutch mechanism 700. Each wing 702 may be operably coupled to its respective plate 706 such that movement of wings 702 causes corresponding movement of plates 706. Tether 726 may include balls 708 spaced along tether 726 similar or identical to embodiments described above. Plates 706 may be positioned such that, in a resting state, the distance between plates 706 at their free ends is less than the diameter of ball 708, but greater than or equal to the diameter of the portions of tether 726 between adjacent balls 708, preventing tether 726 from translating through clutch mechanism 700 when the plates 706 are in their resting or closed position. Wings 702 may be configured such that when wings 702 are pinched or compressed to move the free ends of the wings 702 toward a longitudinal center of the clutch mechanism 700, the free ends of the plates 706 pivot radially outwardly to increase the distance between the plates 706 at their free ends. Movement of the wings 702 may be configured to cause a corresponding increase in distance between plates 706 at their free ends to surpass the diameter of ball 708, allowing tether 726 and associated balls 708 to translate through clutch mechanism 700, uninhibited by plates 706. Each wing 702 may include suture loop 704. Suture loop 704 may loop around wing 702, or a structure attached to wing 702 fit to receive suture loop 704, and extend proximally to be accessible to a surgeon, in a fashion substantially similar to other suture loops described herein. During tensioning of the tether 726, the suture loops 704 may be pulled proximally to compress or pinch the wings 702, and thus increase the distance between the free ends of plates 706. The tether 726 may be tensioned a desired amount, and the force on the wings 702 via suture loops 704 may be reduced so that the plates 706 move back to their resting configuration, inhibiting further movement of the tether 726 via contact between the balls 708 and the plates 706. Suture loops 704 may remain in place until valve 110 has been positioned and desired tension of tether 726 between anchor 210 and prosthetic valve 110 has been achieved. Suture loops 704 may then be released by pulling one end of suture loop 704 proximally until it vacates the patient's body. If it becomes desirable or necessary to adjust the tension of the tether 726 after the suture loops 704 have been removed from the patient, a separate tool may be introduced into the patient to compress or pinch wings 702, allowing for additional adjustment of the tension of the tether 726.

FIG. 32 illustrates valve 110 implanted in heart 234 with anchor 210 seated at or near apex 246 of heart 234. In the illustrated example, desired tension of tether 226 between valve 110 and anchor 210 has been achieved, and excess tether 226 extending proximally from valve 110 is cut and removed from the patient, leaving affixed valve 110 and properly tensioned tether 226 behind.

It should be understood that the ball and flap mechanism 300, the tabbed valve stem 400, the barbed valve stem 500, the guy-line tensioner 600, and the clutch mechanism 700 are all alternative mechanisms for allowing a tether of a prosthetic valve to be tensioned after the prosthetic valve is implanted in a transeptal or other minimally invasive delivery technique that preferably avoids any external puncture of the patient's chest. Each of these mechanisms may be provided on the prosthetic valve 110 without modification of the prosthetic valve 110, or may otherwise replace a portion of the prosthetic valve 110, such as the tether connecting portion 144 of the inner frame 140. Thus, although the prosthetic valve 110 is not described in detail in connection with each of these mechanisms, it should be understood that the mechanisms are intended for use with prosthetic valve 110 and anchor 210, as well as devices similar to prosthetic valve 110 and anchor 210.

According to one aspect of the disclosure, a prosthetic heart valve system comprises:

a prosthetic heart valve having an expandable stent and a prosthetic valve assembly disposed within the stent, the prosthetic valve assembly configured to allow blood to flow in a direction from an inflow end of the stent toward an outflow end of the stent and to substantially block blood from flowing from the outflow end of the stent toward the inflow end of the stent, the prosthetic heart valve including a tether connecting portion;

an anchor adapted to be disposed on or adjacent an epicardial surface of a heart of a patient; and a tether having a distal end coupled to the anchor, the tether extending proximally from the anchor, the tether defining a protrusion having a width greater than portions of the tether adjacent the protrusion, wherein the prosthetic heart valve is configured to be translated along the tether toward the distal end of the tether, the protrusion of the tether configured to engage the tether connecting portion to prevent proximal movement of the prosthetic heart valve relative to the tether; and/or the protrusion is formed by a knot in the tether or a ball on the tether; and/or the tether connecting portion includes a flap hingedly coupled to the tether connecting portion, the flap moveable between an open position in which the prosthetic heart valve may translate distally over the protrusion, and a closed position preventing proximal translation of the prosthetic heart valve over the protrusion relative to the tether; and/or the flap is biased toward the closed position in the absence of applied force; and/or the tether connecting portion includes a tube having two tabs pivotably coupled to the tube, the two tabs having a closed condition in which free ends of the two tabs extend radially inward of the tube; and/or the two tabs each have a second end extending radially outward of the tube in the closed condition, the second ends configured to be compressed to pivot the free ends of the two tabs away from each other to transition the two tabs into an open condition; and/or the two tabs may be biased to the closed condition in the absence of applied force; and/or the two tabs may be formed integrally with the tube and shape set in the closed condition; and/or the tether connecting portion includes a wing hingedly coupled to a plate, the wing having a closed condition in which the plate prevents the tether from translating relative to the prosthetic heart valve, wherein the wing is configured to receive a suture loop operable by a user to move the wing relative to the plate into an open condition in which the plate permits the tether to translate relative to the prosthetic heart valve; and/or the suture loop may be removably coupled to the wing to separate the suture loop from the wing when the tether has a desired tension.

According to another embodiment of the disclosure, a prosthetic heart valve system comprises:

a prosthetic heart valve having an expandable stent and a prosthetic valve assembly disposed within the stent, the prosthetic valve assembly configured to allow blood to flow in a direction from an inflow end of the stent toward an outflow end of the stent and to substantially block blood from flowing from the outflow end of the stent toward the inflow end of the stent, the prosthetic heart valve including a tether connecting portion;

an anchor adapted to be disposed on or adjacent an epicardial surface of a heart of a patient; and a tether having a distal end coupled to the anchor, the tether extending proximally from the anchor, wherein the tether connecting portion includes a stem having a radially expanded condition, a radially collapsed condition, and a barb extending radially inward from the stem, the barb configured to pierce the tether upon transition of the stem from the radially expanded condition to the radially collapsed condition; and/or the stem is configured to expand axially upon transitioning from the radially expanded condition to the radially collapsed condition; and/or the prosthetic heart valve is configured to translate along the tether toward the distal end of the tether while the stem is in the radially expanded condition, and upon transitioning the stem from the radially expanded condition to the radially collapsed condition, the barb is configured to pierce the tether to prevent proximal translation of the prosthetic heart valve relative to the tether.

According to another embodiment of the disclosure, a prosthetic heart valve system comprises:

a prosthetic heart valve having an expandable stent and a prosthetic valve assembly disposed within the stent, the prosthetic valve assembly configured to allow blood to flow in a direction from an inflow end of the stent toward an outflow end of the stent and to substantially block blood from flowing from the outflow end of the stent toward the inflow end of the stent, the prosthetic heart valve including a tether connecting portion;

an anchor adapted to be disposed on or adjacent an epicardial surface of a heart of a patient;

a tether clip; and a tether having a distal end coupled to the tether clip, a proximal end coupled to the tether connecting portion, a first intermediate tether portion looped around the anchor, and a second intermediate tether portion, wherein the second intermediate tether portion may be threaded through an aperture in the tether clip, the tether clip configured to slide along the second intermediate tether portion to adjust a tension of the tether; and/or the tether clip is configured to receive at least one suture loop operable by a user to slide the tether clip along the second intermediate tether portion.

According to another embodiment of the disclosure, a method of implanting a prosthetic heart valve comprises:

positioning an anchor adjacent a ventricular wall while a tether is coupled to and extends proximally from the anchor;

advancing the prosthetic heart valve distally along the tether while the anchor is positioned adjacent the ventricular wall;

deploying the prosthetic heart valve into a native valve annulus;

pulling the tether in a proximal direction to tension the tether; and fixing the prosthetic heart valve to the tether while the tether is tensioned; and/or the tether defines a protrusion having a width greater than portions of the tether adjacent the protrusion; and/or the prosthetic heart valve is advanced distally along the tether, wings on a tether connecting portion of the prosthetic heart valve are compressed to allow the protrusion to pass through the tether connecting portion, and fixing the prosthetic heart valve to the tether includes releasing compression of the wings to prevent the protrusion from passing through the tether connecting portion; and/or the prosthetic heart valve includes a tether connecting portion including a tube having two tabs pivotably coupled to the tube, the two tabs having a closed condition in which free ends of the two tabs extend radially inward of the tube, and as the prosthetic heart valve is advanced distally along the tether past the protrusion, the two tabs pivot to create clearance for the protrusion; and/or the prosthetic heart valve includes a flap hingedly coupled to a tether connecting portion, and while pulling the tether in a proximal direction to tension the tether, the protrusion contacts the flap causing the flap to transition to an open condition allowing the protrusion to pass through the tether connecting portion; and/or the proximal end of the tether is coupled to a tensioning mechanism while pulling the tether in the proximal direction; and/or the method further comprises cutting the tether at a point proximal to a location on the tether where the tether is fixed to the prosthetic heart valve.

Although the invention herein has been described with reference to particular embodiments, it is to be understood that these embodiments are merely illustrative of the principles and applications of the present invention. For example, although embodiments of prosthetic valves are described herein in the context of prosthetic mitral valves, the disclosure may substantially similarly apply to prosthetic tricuspid valves, with or without modifications. It is therefore to be understood that numerous modifications may be made to the illustrative embodiments and that other arrangements may be devised without departing from the spirit and scope of the present invention as defined by the appended claims.

The invention claimed is:

1. A prosthetic heart valve system comprising:
    a prosthetic heart valve having an expandable frame assembly including an inner frame and an outer frame, and a prosthetic valve assembly disposed within the inner frame, the prosthetic valve assembly configured to allow blood to flow in a direction from an inflow end of the inner frame toward an outflow end of the inner frame and to block blood from flowing from the outflow end of the inner frame toward the inflow end of the inner frame, the inner frame including a tether connecting portion, wherein the inner frame includes a plurality of struts that extend radially inwardly toward a radial center of the inner frame, the tether connecting portion being coupled to the plurality of struts so that the tether connecting portion is positioned at the radial center of the inner frame;

an anchor adapted to be disposed on or adjacent an epicardial surface of a heart of a patient; and a tether having a distal end fixedly coupled to the anchor, the tether extending proximally from the anchor, the tether defining a protrusion having a width greater than portions of the tether adjacent the protrusion, wherein the tether extends through the tether connection portion and is slidably coupled to the tether connection portion so that the prosthetic heart valve can translate along the tether toward the distal end of the tether while the distal end of the tether is fixedly coupled to the anchor, the protrusion of the tether configured to engage the tether connecting portion to prevent proximal movement of the prosthetic heart valve relative to the tether, wherein the tether connecting portion includes a flap hingedly coupled to the tether connecting portion, the flap moveable between an open position in which the prosthetic heart valve may translate distally over the protrusion, and a closed position preventing proximal translation of the prosthetic heart valve over the protrusion relative to the tether, the tether connection portion including a stem body that includes a rim, the flap abutting and contacting the rim in the closed position, the flap spaced away from the rim in the open position.

2. The prosthetic heart valve system of claim 1, wherein the protrusion is formed by a knot in the tether or a ball on the tether.

3. The prosthetic heart valve system of claim 1, wherein the flap is biased toward the closed position in the absence of applied force.

4. The prosthetic heart valve system of claim 1, wherein in the closed position of the flap, the flap sits perpendicular to a central longitudinal axis of the tether connecting portion, and the tether extends through the flap.

5. The prosthetic heart valve system of claim 4, wherein in the open position of the flap, the tether extends through the flap.

6. The prosthetic heart valve system of claim 4, wherein the flap has a free end opposite an end of the flap that is hingedly coupled to the tether connecting portion, the free end having a circular circumference that is interrupted by a "U"-shaped recessed portion.

7. The prosthetic heart valve system of claim 6, wherein two free arms of the flap define portions of the "U"-shaped recessed portion.

8. The prosthetic heart valve system of claim 7, wherein the "U"-shaped recessed portion has a width defined between inner edges of the two free arms, the width of the "U"-shaped recessed portion being greater than a diameter of the tether, but smaller than a diameter of the protrusion.

9. The prosthetic heart valve system of claim 6, wherein in the closed position of the flap, the tether extends through the "U"-shaped recessed portion of the flap.

10. The prosthetic heart valve system of claim 9, wherein in the open position of the flap, the tether extends through the "U"-shape recessed portion of the flap.

11. A method of implanting a prosthetic heart valve system, the method comprising:

positioning an anchor adjacent a ventricular wall while a distal end of a tether is fixedly coupled to and extends proximally from the anchor, the anchor being adapted to be disposed on or adjacent an epicardial surface of a heart of a patient, the tether defining a protrusion having a width greater than portions of the tether adjacent the protrusion;

advancing the prosthetic heart valve distally along the tether while the anchor is positioned adjacent the ventricular wall, the prosthetic heart valve having an expandable frame assembly including an inner frame and an outer frame, and a prosthetic valve assembly disposed within the inner frame, the prosthetic valve assembly configured to allow blood to flow in a direction from an inflow end of the inner frame toward an outflow end of the inner frame and to block blood from flowing from the outflow end of the inner frame toward the inflow end of the inner frame, the prosthetic heart valve including a tether connecting portion, wherein the inner frame includes a plurality of struts that extend radially inwardly toward a radial center of the inner frame, the tether connecting portion being coupled to the plurality of struts so that the tether connecting portion is positioned at the radial center of the inner frame;

deploying the prosthetic heart valve into a native valve annulus;

pulling the tether in a proximal direction to tension the tether, the tether extending through the tether connection portion and being slidably coupled to the tether connection portion so that the prosthetic heart valve can translate along the tether toward the distal end of the tether while the distal end of the tether is fixedly coupled to the anchor, the protrusion of the tether configured to engage the tether connecting portion to prevent proximal movement of the prosthetic heart valve relative to the tether; and fixing the prosthetic heart valve to the tether while the tether is tensioned, wherein the tether connecting portion includes a flap hingedly coupled to the tether connecting portion, the flap moveable between an open position in which the prosthetic heart valve may translate distally over the protrusion, and a closed position preventing proximal translation of the prosthetic heart valve over the protrusion relative to the tether, the tether connection portion including a stem body that includes a rim, the flap abutting and contacting the rim in the closed position, the flap spaced away from the rim in the open position.

12. The method of claim 11, wherein while pulling the tether in the proximal direction to tension the tether, the protrusion contacts the flap causing the flap to transition to the open position allowing the protrusion to pass through the tether connecting portion.

13. The method of claim 11, wherein a proximal end of the tether is coupled to a tensioning mechanism while pulling the tether in the proximal direction.

14. The method of claim 11, further comprising cutting the tether at a point proximal to a location on the tether where the tether is fixed to the prosthetic heart valve.

* * * * *